(12) United States Patent
Mihan et al.

(10) Patent No.: US 8,227,557 B2
(45) Date of Patent: Jul. 24, 2012

(54) IRON COMPLEXES AND THEIR USE IN POLYMERIZATION PROCESSES

(75) Inventors: Shahram Mihan, Bad Soden (DE); Fabiana Fantinel, Frankfurt (DE); Reynald Chevalier, Frankfurt (DE); Harald Schmitz, Weinheim (DE)

(73) Assignee: Basell Polyolefine GmbH, Wesseling (DE)

( * ) Notice: Subject to any disclaimer, the term of this patent is extended or adjusted under 35 U.S.C. 154(b) by 432 days.

(21) Appl. No.: 12/448,997

(22) PCT Filed: Mar. 1, 2008

(86) PCT No.: PCT/EP2008/001642
§ 371 (c)(1),
(2), (4) Date: Jul. 17, 2009

(87) PCT Pub. No.: WO2008/107135
PCT Pub. Date: Sep. 12, 2008

(65) Prior Publication Data
US 2010/0087607 A1 Apr. 8, 2010

Related U.S. Application Data

(60) Provisional application No. 60/918,501, filed on Mar. 16, 2007.

(30) Foreign Application Priority Data

Mar. 6, 2007 (EP) .................................. 07004547

(51) Int. Cl.
C08F 4/80 (2006.01)
C08F 4/70 (2006.01)
C08F 4/60 (2006.01)
C07F 15/02 (2006.01)

(52) U.S. Cl. ............ 526/172; 526/161; 526/169.1; 526/160; 526/170; 526/904; 526/352; 526/348; 556/138

(58) Field of Classification Search .......... 526/172, 526/161; 556/138
See application file for complete search history.

(56) References Cited

U.S. PATENT DOCUMENTS

| | | | |
|---|---|---|---|
| 3,242,150 A | 3/1966 | Scoggin | |
| 3,248,179 A | 4/1966 | Norwood | |
| 5,153,157 A | 10/1992 | Hlatky et al. | |
| 5,324,800 A | 6/1994 | Welborn, Jr. et al. | |
| 5,372,980 A | 12/1994 | Davis | |
| 5,565,534 A | 10/1996 | Aulbach et al. | |
| 5,698,642 A | 12/1997 | Govoni et al. | |
| 5,703,187 A | 12/1997 | Timmers | |
| 5,710,297 A | 1/1998 | Weller et al. | |
| 5,770,753 A | 6/1998 | Küber et al. | |
| 5,840,948 A | 11/1998 | Rohrmann et al. | |
| 6,087,291 A | 7/2000 | Speca et al. | |
| 6,160,145 A | 12/2000 | Wu et al. | |
| 6,417,302 B1 | 7/2002 | Bohnen | |
| 6,423,848 B2 * | 7/2002 | Bennett | 546/329 |
| 6,455,660 B1 | 9/2002 | Clutton et al. | |
| 6,548,442 B1 | 4/2003 | McDaniel et al. | |
| 6,589,905 B1 | 7/2003 | Fischer et al. | |
| 6,620,953 B1 | 9/2003 | Bingel et al. | |
| 6,645,901 B2 * | 11/2003 | Goto et al. | 502/104 |
| 2001/0000519 A1 | 4/2001 | Bennett | |
| 2007/0213205 A1 | 9/2007 | Mihan | |

FOREIGN PATENT DOCUMENTS

| | | |
|---|---|---|
| WO | WO 91/09882 | 7/1991 |
| WO | WO 2004/074333 | 9/2004 |
| WO | WO 2004/074333 A2 * | 9/2004 |

OTHER PUBLICATIONS

Bouwkamp et al., Inorg. Chem., 2006, 46, 2-4.*
Scott et al., J. Am. Chem. Soc., 2005, 127, 13019-13029.*
Fieser et al. "Heterocyclen," *Lehrbuch der Organischen Chemie*, 3rd Revised Edition, Verlag Chemie, Weinheim, (1957), pp. 921, 931-933,936-938, 942.
Falbe, J. & Regitz, M. *Römp Chemie Lexikon*, $9^{th}$ Edition, Thieme 1992, New York 6, pp. 5128-5129.
Weinsenfeldt et al., "ansa-Metallocene derivatives; Racemic and meso diastereomers of group IV metallocene derivatives with symmetrically substituted, dimethylsilanediyl-bridged ligand framewors. Crystal structure of R, S-$Me_2Si(3$-t-Bu-5-$MeC_5H_2)_2ZrCl_2$," *Journal of Organometallic Chemistry*, 369, (1989), 359-370.
Vidyaratne et al. "Reactivity of Chromium Complexes of a Bis(imino)pyridine Ligand: Highly Active Ethylene Polymerization Catalysts Carrying the Metal in a Formally Low Oxidation State," Organometallics, 26, (2007), 3201-3211.
Reardon et al. "Mono- and Zerovalent Manganese Alkyl Complexes Supported by the $\alpha,\alpha'$-Diiminato Pyradine Ligand: Alkyl Stabilization at the Expense of Catalytic Performance," *Organometallics*, 21, (2002), 786-788.
Kooistra et al., "Chemical ligand non-innocence in pyridine diimine Rh complexes," *Inorganica Chimica Acta*, 357 (2004) 2945-2952.
Scott et al., "Multiple Pathways for Dinitrogen Activation during the Reduction of an Fe Bis(iminepyridine) Complex," *Inorganic Chemistry*, vol. 47 No. 3, (2008), 896-911.
Bouwkamp et al. "Bis(imino)pyridine Ligand Deprotonation Promoted by a Transient Iron Amide," *Inorganic Chemistry*, vol. 45 No. 1, (2006), 2-4.
Sugiyama et al. "Preparation of an Active Neodymium Catalyst for Regioselective Butadiene *cis*-Polymerization Supported by a Dianionic Modification of the 2,6-Diiminopyridine Ligand," *Organometallics*, 23, (2004) 5054-5061.
Scott et al. "Metal versus Ligand Alkylation in the Reactivity of the (Bis-iminopyridinato)Fe Catalyst," *Journal of American Chemical Society*, 127, (2005) 13109-13029.

* cited by examiner

*Primary Examiner* — Rip A. Lee
(74) *Attorney, Agent, or Firm* — Dilworth IP LLC

(57) ABSTRACT

Specific iron complexes (A), a catalyst system for polymerization of olefins comprising at least one metal complex (A) and/or (A'), a prepolymerized catalyst system, the use of these catalyst systems for the polymerization of olefins, and a process for the preparation of polyolefins by polymerization or copolymerization of olefins in the presence of one of the described catalyst systems.

17 Claims, No Drawings

IRON COMPLEXES AND THEIR USE IN POLYMERIZATION PROCESSES

CROSS-REFERENCE TO RELATED APPLICATIONS:

This application is a national phase filing under 35 U.S.C. §371 of International Application PCT/EP2008/001642, filed 1 Mar. 2008, claiming priority to European Patent Application 07 004 547.1 filed 6 Mar. 2007 and provisional U.S. Appl. No. 60/918,501 filed 16 Mar. 2007; the disclosures of International Application PCT/EP2008/001642, European Pat. Appl. 07 004 547.1, and U.S. Appl. No. 60/918,501, each as filed, are incorporated herein by reference.

FIELD OF THE INVENTION

The present invention relates to specific iron complexes (A), a catalyst system for polymerization of olefins comprising at least one metal complex (A) and/or (A'), a prepolymerized catalyst system, the use of these catalyst systems for the polymerization of olefins, and a process for the preparation of polyolefins by polymerization or copolymerization of olefins in the presence of one of the described catalyst systems.

Since years the person skilled in the art knows the use of transition metal compounds as catalysts in polymerization and copolymerization of unsaturated compounds. The use of transition metal catalysts, i.e. metallocenes, shows a great influence on the preparation of polyolefins, since it opens up access to novel polyolefinic materials or to materials having improved properties. Therefore, there is great interest in the development of novel families of catalysts for the polymerization of unsaturated compounds in order to achieve an even better control over the properties of polyolefins or further novel products. In particular, the use of transition metal catalysts with late transition metals is of interest because of their property of tolerating heteroatom functionalities.

PRIOR ART

Transition metal complexes without cyclopentadienyl ligands have also been tested for some years. WO 04/074333 describes among others 2,6-bis(1-(2,6-diisopropylphenylamido)ethylidene)-pyridine complexes of yttrium, lanthanide and actinide metals as catalysts for the polymerization of conjugated dienes. WO 98/27124 describes 2,6-bis(imino)pyridyl iron and cobalt complexes as catalysts for the homo and copolymerization of ethylene. WO 99/46302 describes a catalyst composition for the polymerization of 1-olefins based on (a) a 2,6-bis(imino)pyridyl iron component and (b) a further catalyst, i.e. a zirkonocene or Ziegler catalyst. The preparation of several (bis-iminopyridinato) iron catalysts and a comparison of their reactivities during polymerization of ethylene are described in J. Am. Chem. Soc. 2005, 127, 13019-13029. A 2,6-bis(1-(2,6-diisopropylphenylamido)ethylidene)pyridine iron complex is disclosed providing a bimodal polymer comprising in nearly the same amounts one component having low molecular weight and narrow molecular weight distribution and a second component having high molecular weight and broad molecular weight distribution. Furthermore, this article describes a 2-(1-2,6-diisopropylphenylamido)ethylidene)-6-(1-(2,6-diisopropylphenylimino)ethyl pyridine iron complex providing solely a polyethylene with high molecular weight and broad molecular weight distribution. WO 05/103096 discloses a catalyst composition based on (a) a 2,6-bis(imino)pyridyl iron component and (b) a further catalyst, i.e. a hafnocene catalyst.

SUMMARY OF THE INVENTION

It was an object of the present invention to provide new catalysts for the polymerization of olefins, especially for the homo-and copolymerization of ethylene, and a new polymerization process for the preparation of these polymers.

It has surprisingly been found that this object can be achieved by using specific iron complexes (A) according to claim 1, by a specific catalyst system according to claim 6, which catalyst system can be prepolymerized, and by the use of these catalyst systems for polymerization and copolymerization of olefins. Furthermore, a process for the preparation of polyolefins has been found using one of the described catalysts systems.

The iron complexes (A) of the invention are described in formula (I)

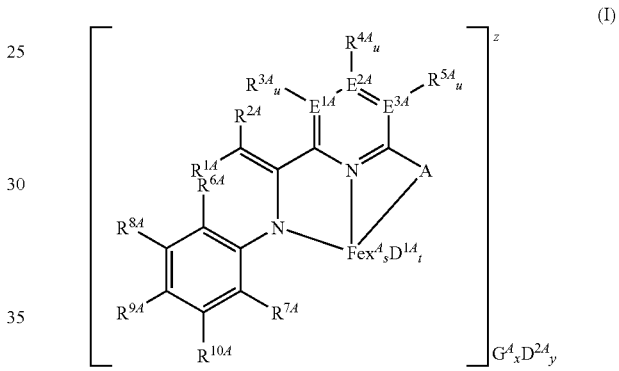

wherein the variables have the following meaning:

A is

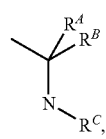

A1

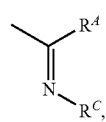

A2

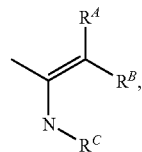

A3

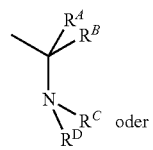

A4 oder

-continued

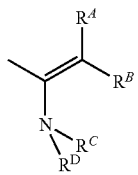

A5

$R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11}_3$, wherein the organic radicals $R^{1A}$-$R^{2A}$ can also be substituted by halogens, and/or two radicals $R^{1A}$-$R^{2A}$ can also be bonded with one another to form a five-or six-membered ring, $R^{3A}$-$R^{10A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six-or seven-membered ring and/or in each case two radicals $R^{3A}$-$R^{5A}$ and/or in each case two radicals $R^{6A}$-$R^{10}$ are bonded with one another to form a five-, six-or seven-membered heterocyclyl, which comprises at least one atom from the group consisting of N, P, O or S, wherein at least one of the radicals $R^{6A}$-$R^{10A}$ is selected from the group consisting of chlorine, bromine, iodine, $CF_3$ or $OR^{12A}$.

$R^{11A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, and/or two radicals $R^{11A}$ can also be bonded with one another to form a five-or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five-or six-membered ring, $R^A$,$R^B$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^A$,$R^B$ can also be substituted by halogens, and/or in each case two radicals $R^A$,$R^B$ can also be bonded with one another to form a five-or six-membered ring, $R^C$, $R^D$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R_C$,$R^D$ can also be substituted by halogens, and/or in each case two radicals $R^C$, $R^D$ can also be bonded with one another to form a five-or six-membered ring, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1 to 10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, $CN$, $SCN$, β-diketonate, $CO$, $BF_4^-$, $PF_6^-$ or bulky non-coordinating anions, wherein the organic radicals $X^A$ can also be substituted by halogens and/or at least one radical $R^{13A}$, and the radicals $X^A$ are optionally bonded with one another, $R^{13A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogens, and/or in each case two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, wherein the organic radicals $R^{14A}$ can also be substituted by halogens, and/or in each case two radicals $R^{14A}$ can also be bonded with one another to form a five-or six-membered ring, s is 1, 2, 3 or 4, $D^{1A}$, $D^{2A}$ is a neutral donor, t, y is 0 to 4, $G^A$ is a simply positively charged cation, x is 0, 1 or 2, and z is 0, −1 or −2.

The radicals $R^{1A}$-$R^{2A}$ can be varied within a wide range. Possible carboorganic substituents $R^{1A}$-$R^{2A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3, 4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two radicals $R^{1A}$-$R^{2A}$ may also be joined to form a 5-, 6-or 7-membered ring and/or two radicals $R^{1A}$-$R^{2A}$ may be joined to form a five-, six-or seven-membered heterocycle containing at least one atom from the group consisting of N, P, O and S and/or the organic radicals $R^{1A}$-$R^{2A}$ may also be substituted by halogens such as fluorine, chlorine or bromine. Furthermore, $R^{1A}$-$R^{2A}$ can also be $SiR^{11A}_3$. The radicals $R^{11A}$ are more fully described below. Si-organic radicals may be for example trimethylsilyloxy, triethyl-silyloxy, butyldimethylsilyloxy, tributylsilyloxy or tri-tert-butylsilyloxy, triallylsilyloxy, triphenylsilyloxy, or dimethylphenylsilyloxy. Preferred radicals $R^{1A}$-$R^{2A}$ are hydrogen, methyl, ethyl, n-propyl, isopropyl, n-butyl, isobutyl, tert-butyl, n-pentyl, n-hexyl, n-heptyl, n-octyl, benzyl, phenyl, ortho dialkyl-or dichloro substituted phenyl, trialkyl-or trichloro substituted phenyl, naphthyl, biphenyl, and anthranyl, especially hydrogen and methyl. Preferably $R^{1A}$-$R^{2A}$ are identical.

The radicals $R^{3A}$-$R^{10A}$ can be varied within a wide range, wherein at least one of the radicals $R^{6A}$-$R^{10A}$ is selected from the group consisting of chlorine, bromine, iodine, $CF_3$ or $OR^{12A}$. Possible carboorganic substituents $R^{3A}$-$R^{10}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two vicinal radicals $R^{3A}$-$R^{5A}$ and/or two vicinal radicals $R^{5A}$-$R^{10}$ may also be joined to form a 5-, 6-or 7-membered ring and/or two vicinal radicals $R^{3A}$-$R^{5A}$ and/or two vicinal radicals $R^{6A}$-$R^{10A}$ may be joined to form a five-, six-or seven-membered heterocycle containing at least one atom from the group consisting of N, P, O and S. The organic radicals $R^{3A}$-$R^{10A}$ may also be substituted by halogens such as fluorine, chlorine or bromine, by amino $NR^{12A}{}_2$, by alkoxy and/or aryloxy $OR^{12A}$, for example dimethylamino, N-pyrrolidinyl, picolinyl, methoxy, ethoxy, or by Si-organic radicals $SiR^{11A}{}_3$. Further radicals $R^{3A}$-$R^{10}$ are amino $NR^{12A}{}_2$, alkoxy and/or aryloxy $OR^{12A}$, halogen, and/or $SiR^{11A}{}_3$. The radicals $R^{11A}$ and $R^{12A}$ are more fully described below, wherein the radicals $Si R^{11A}{}_3$ may also be bonded to $E^{1A}$-$E^{3A}$ via an oxygen or nitrogen atom. Examples for possible radicals $R^{3A}$-$R^{10}$ are dimethylamino, N-pyrrolidinyl, picolinyl, methoxy, ethoxy, isopropoxy, fluorine, chlorine, bromine or iodine. Si-organic radicals are for example trimethylsilyloxy, triethylsilyloxy, butyldimethylsilyloxy, tributylsilyloxy or tri-tert-butylsilyloxy, triallylsilyloxy, triphenylsilyloxy, or dimethylphenylsilyloxy.

Preferred radicals $R^{3A}$-$R^{5A}$ are hydrogen, methyl, trifluoromethyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl-or -dichloro-substituted phenyls, trialkyl-or trichloro-substituted phenyls, naphthyl, biphenyl and anthranyl. Particularly preferred organosilicon substituents are trialkylsilyl groups having from 1 to 10 carbon atoms in the alkyl radical, in particular trimethylsilyl groups.

Preferred radicals $R^{6A}$-$R^{10}$ are hydrogen, methyl, trifluoromethyl, ethyl, n-propyl, isopropyl, n-butyl, isobutyl, tert-butyl, n-pentyl, n-hexyl, n-heptyl, n-octyl, vinyl, allyl, benzyl, phenyl, fluorine, chlorine, or bromine, especially hydrogen, wherein at least one of the radicals $R^{6A}$-$R^{10A}$ is selected from the group consisting of chlorine, bromine, iodine, $CF_3$ or $OR^{12A}$.

Preferred radicals $R^{6A}$, $R^{7A}$ and $R^{9A}$ are, methyl, trifluoromethyl, ethyl, n-propyl, isopropyl, n-butyl, isobutyl, tert-butyl, n-pentyl, n-hexyl, n-heptyl, n-octyl, vinyl, allyl, benzyl, phenyl, fluorine, chlorine, or bromine. Especially preferred radicals for $R^{6A}$ and/or $R^{9A}$ are $C_1$-$C_{22}$-alkyl, which can be substituted by halogen, especially $C_1$-$C_{22}$-n-alkyl, which can be substituted by halogen, i.e. methyl, trifluoromethyl, ethyl, n-propyl, n-butyl, n-pentyl, n-hexyl, n-heptyl, n-octyl, vinyl, wherein $R^{7A}$ is halogen such as fluorine, chlorine or bromine, especially chlorine, or $R^{7A}$ and/or $R^{9A}$ is $C_1$-$C_{22}$-alkyl, which can be substituted by halogen, especially $C_1$-$C_{22}$-n-alkyl, which can be substituted by halogen, i.e. methyl, trifluoromethyl, ethyl, n-propyl, n-butyl, n-pentyl, n-hexyl, n-heptyl, n-octyl, vinyl, wherein $R^{6A}$ is halogen such as fluorine, chlorine or bromine, especially chlorine. Preferred radicals $R^{6A}$ and $R^{10A}$ are hydrogen, methyl, ethyl, n-propyl, fluorine, chlorine and bromine, especially hydrogen. Especially preferred radicals $R^{6A}$-$R^{10A}$ are: $R^{6A}$ and $R^{9A}$ are independently of one another hydrogen, methyl, ethyl, n-propyl und iso-propyl, especially methyl, $R^{8A}$ and $R^{10A}$ are independently of one another hydrogen, methyl, ethyl, and n-propyl, preferably both hydrogen, and $R^{7A}$ is fluorine, chlorine or bromine, especially chlorine.

The number u of the radicals $R^{3A}$-$R^{5A}$ depends on whether $E^1$-$E^3$ is nitrogen or carbon. If a radical $E^{1A}$-$E^{3A}$ is nitrogen, u is 0 for the corresponding radical $R^{3A}$-$R^{5A}$. If a radical $E^{1A}$-$E^{3A}$ is carbon, u is 1 for the corresponding radical $R^{3A}$-$R^{5A}$.

The three atoms $E^{1A}$-$E^{3A}$ in a molecule can be identical or different. They are preferably nitrogen or carbon, in particular carbon.

The radicals $R^{11A}$ und $R^{12A}$ can be varied within a wide range. Possible carboorganic substituents $R^{11A}$ und $R^{12A}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two radicals $R^{11A}$ and/or two radicals $R^{12A}$ may also be joined to form a 5-, 6-or 7-membered ring and/or a five-, six-or seven-membered heterocycle containing at least one atom from the group consisting of N, P, O and S. Furthermore, the organic radicals $R^{11A}$ und $R^{12A}$ may also be substituted by halogens such as fluorine, chlorine or bromine, especially chlorine The radical A can have the following meaning:

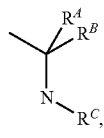

A1

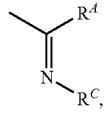

A2

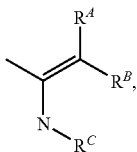

A3

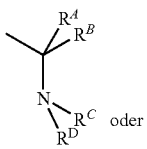

A4

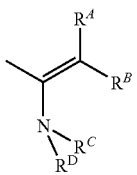

A5

The radicals $R^A$ und $R^B$ can be independently of one another varied within a wide range. Possible carboorganic substituents are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two radicals $R^A$ und $R^B$ may also be joined to form a 5-, 6-or 7-membered ring and/or a five-, six-or seven-membered heterocycle containing at least one atom from the group consisting of N, P, O and S. Furthermore, the organic radicals $R^A$ und $R^B$ may also be substituted by halogen such as fluorine, chlorine or bromine, especially chlorine. Suitable Si-organic radicals $SiR^{11A}_3$ as radicals $R^A$ und $R^B$ are the same C-organic radicals as described in more detail for $R^{1A}$-$R^{2A}$, wherein two radicals may be joined to form a 5-, 6-or 7-membered ring, for example trimethylsilyloxy, triethylsilyloxy, butyldimethylsilyloxy, Tributylsilyloxy, tri-tert-butylsilyloxy, triallylsilyloxy, triphenylsilyloxy, or dimethylphenylsilyloxy.

Also the radicals $R^C$ and $R^D$ can be independently of one another varied within a wide range. Possible carboorganic substituents are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two radicals $R^C$ and $R^D$ may also be joined to form a 5-, 6-or 7-membered ring and/or a five-, six-or seven-membered heterocycle containing at least one atom from the group consisting of N, P, O and S. Furthermore, the organic radicals $R^C$ and $R^D$ may also be substituted by halogens such as fluorine, chlorine or bromine, especially chlorine. Suitable Si-organic radicals $SiR^{11A}_3$ as radicals $R^C$ and $R^D$ are the same C-organic radicals as described in more detail for $R^{1A}$-$R^{2A}$, wherein two radicals $R^C$ and $R^D$ may be joined to form a 5-, 6-or 7-membered ring, for example trimethylsilyloxy, triethylsilyloxy, butyldimethylsilyloxy, tributylsilyloxy, tri-tert-butylsilyloxy, triallylsilyloxy, triphenylsilyloxy, or dimethylphenylsilyloxy.

Preferably the radicals A2 and A3 are used. Especially, iron complexes comprising radical A2 are suitable for the present invention.

The ligands $X^A$ can be independently of one another varied within a wide range. They are for example predetermined by the corresponding metal starting compound used for the synthesis of the iron complexes. But they may also be changed afterwards. Possible ligands $X^A$ are, in particular, halogens such as fluorine, chlorine, bromine, iodine, especially chlorine, and also hydrogen, $C_1$-$C_{10}$-alkyl, wherein the alkyl may be linear, cyclic or branched, $C_2$-$C_{10}$-alkenyl, wherein the alkenyl may be linear, cyclic, or branched and in which the double bond may be internal or terminal, $C_6$-$C_{20}$-aryl, wherein the aryl may be substituted by further alkyl groups, or alkylaryl having 1-10 carbon atoms in the alkyl part and 6 to 20 carbon atoms in the aryl part, wherein the organic radicals $X^A$ can also be substituted by halogens and/or at least one radical $R^{13A}$. Furthermore, $NR^{13C}_2$, $OR^{13C}$, $SR^{13C}$, $SO_3R^{13C}$, $OC(O)R^{13C}$, CN, SCN, β-diketonate, CO, $BF_4^-$, $PF_6^-$ or a bulky noncoordinating anion such as $B(C_6F_5)_4^-$ may be used. Especially preferred ligands $X^A$ are methyl, ethyl, propyl, butyl, vinyl, allyl, phenyl, benzyl or —$CH_2$—$Si(CH_3)_3$. Some of the substituted ligands are especially preferred, since they can be obtained from cheap and readily available starting materials. Thus, a particularly preferred embodiment is that in which $X^A$ is dimethylamide, methoxide, ethoxide, isopropoxide, phenoxide, naphthoxide, triflate, p-toluenesulfonate, acetate or acetylacetonate.

The number s of the ligands $X^A$ depends on the oxidation state of the iron. The number s can thus not be given in general terms. The oxidation state of the iron in catalytically active complexes is usually known to those skilled in the art. However, it is also possible to use complexes whose oxidation state does not correspond to that of the active catalyst. Such complexes can then be appropriately reduced or oxidized by means of suitable activators. Usually, s is 1, 2, 3, or 4. Preference is given to using iron complexes in the oxidation state +3 or +2.

The radicals $R^{13A}$ can be independently of one another varied within a wide range. Possible carboorganic substituents are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4, 5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two radicals $R^{13A}$ may also be joined to form a 5-, 6-or 7-membered ring and/or a five-, six-or seven-membered heterocycle containing at least one atom from the group consisting of N, P, O and S. Furthermore, the organic radicals $R^{13A}$ may also be substituted by halogens such as fluorine, chlorine or bromine, especially chlorine. The radicals $R^{13A}$ may also be $SiR^{14A}_3$, wherein $R^{14A}$ has the same meaning as the radicals $R^{11A}$ described above, i.e. trimethylsilyloxy, triethylsilyloxy, butyldimethylsilyloxy, Tributylsilyloxy, tri-tert-butylsilyloxy, triallylsilyloxy, triphenylsilyloxy, or dimethylphenylsilyloxy.

$D^{1A}$ and $D^{2A}$ are independently of one another an uncharged donor, in particular an uncharged Lewis base or Lewis acid, for example amines, alcohols, ethers, ketones, aldehydes, esters, sulfides or phosphines which may be bound to the iron centre or else still be present as residual solvent from the preparation of the iron complexes.

The number t of the ligands $D^{1A}$ and the number y of the ligands $D^{2A}$ are independently of one another from 0 to 4 and are often dependent on the solvent in which the iron complex is prepared and the time for which the resulting complexes are dried and can therefore also be a nonintegral number such as 0.5 or 1.5. In particular, t and y are 0, 1 to 2.

$G^A$ is a simply positively charged cation such as lithium, natrium or kalium, preferably lithium.

The number x of the simply positively charged cations can be 0, 1, or 2 and depends, just like the number s of the ligands $X^A$, on the oxidation state of the iron and on the preparation conditions of the iron complex. Preferably, x is 0 for A being A1, A2, A3, A4, or A5 and the iron being in the oxidation state +3. Preferably, if the iron is in the oxidation state +2, x is 0 for A being A2, A4, or A5, and x is 1 for A being A1 or A3.

The number z of the complex (A) can be 0, −1, or −2 and depends, just like the number s of the ligands $X^A$, on the oxidation state of the iron and on the preparation conditions of the iron complex. Preferably, z is 0 for A being A1, A2, A3, A4, or A5 and the iron being in the oxidation state +3. Preferably, if the iron is in the oxidation state +2, z is 0 for A being A2, A4, or A5, and z is −1 for A being A1 or A3.

Preferred iron complexes (A) of the invention are those of formula (Ia)

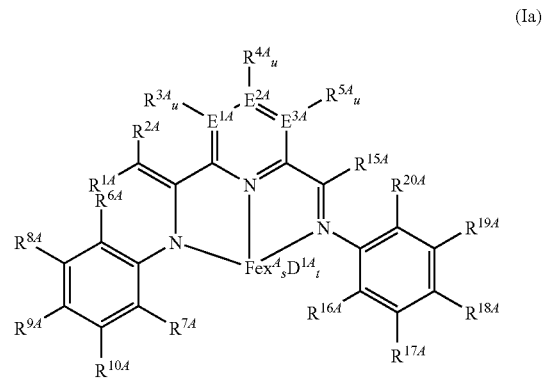

(Ia)

wherein the variables have the following meaning:
$R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11}_3$, wherein the organic radicals $R^{1A}$-$R^{2A}$ can also be substituted by halogens, and/or two radicals $R^{1A}$-$R^{2A}$ can also be bonded with one another to form a five-or six-membered ring, $R^{3A}$-$R^{10A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six-or seven-membered ring and/or in each case two radicals $R^{3A}$-$R^{5A}$ and/or in each case two radicals $R^{6A}$-$R^{10A}$ are bonded with one another to form a five-, six-or seven-membered heterocyclyl, which comprises at least one atom from the group consisting of N, P, O or S, wherein at least one of the radicals $R^{6A}$-$R^{10A}$ is selected from the group consisting of chlorine, bromine, iodine, $CF_3$ or $OR^{12A}$, $R^{11A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, and/or two radicals $R^{11A}$ can also be bonded with one another to form a five-or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five-or six-membered ring, $R^{15A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^{15}$ can also be substituted by halogens, $R^{16A}$-$R^{20A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{16A}$-$R^{20A}$ can also be substituted by halogens, $NR^{12A}_2$, $OR^{12A}$ or $SiR^{11A}_3$ and/or two radicals $R^{16A}$-$R^{20A}$ can also be bonded with one another to form a five-, six-or seven-membered ring and/or to form a five-, six-or seven-membered heterocyclyl, which comprises at least one atom from the group consisting of N, P, O or S, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, CN, SCN, β-diketonate, CO, $BF_4^-$, $PF_6^-$ or bulky non-coordinating anions, wherein the organic radicals $X^A$ can also be substituted by halogens and/or at least one radical $R^{13A}$, and the radicals $X^A$ are optionally bonded with one another, $R^{13A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogen, and/or two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, wherein the organic radicals $R^{14A}$ can also be substituted by halogens, and/or two radicals $R^{14A}$ can also be bonded with one another to form a five-or six-membered ring, s is 1, 2, 3 or 4, t is 0 to 4, and $D^{1A}$ is a neutral donor.

The embodiments and preferred embodiments described above likewise apply to $E^{1A}$-$E^{3A}$, $R^{1A}$-$R^{2A}$, $R^{3A}$-$R^{10A}$, $R^{11A}$-$R^{14A}$, $D^{1A}$, $X^A$, s, t, and u.

The radicals $R^{15A}$ can be independently of one another varied within a wide range. Possible carboorganic substituents are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, and/or the organic radicals $R^{15A}$ may also be substituted by halogens such as fluorine, chlorine or bromine. The radicals $R^{15A}$ may also be $SiR^{11A}_3$. The radicals $R^{11A}$ have the same meaning as described above, i.e. trimethylsilyloxy, triethylsilyloxy, butyldimethylsilyloxy, tributylsilyloxy, tri-tert-butylsilyloxy, triallylsilyloxy, triphenylsilyloxy, or dimethylphenylsilyloxy.

Preferred radicals $R^{15A}$ are hydrogen, methyl, ethyl, n-propyl, iso-propyl, n-butyl, iso-butyl, tert.-butyl, n-pentyl, n-hexyl, n-heptyl, n-octyl, benzyl, phenyl, ortho dialkyl-or dichlorosubstituted phenyl, trialkyl-or trichlorosubstituted phenyl, naphthyl, biphenyl and anthranyl.

The radicals $R^{16A}$-$R^{20A}$ can be varied within a wide range. Possible carboorganic substituents $R^{16A}$-$R^{20A}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two vicinal radicals $R^{16A}$-$R^{20A}$ may also be joined to form a 5-, 6-or 7-membered ring and/or two vicinal radicals $R^{16A}$-$R^{20A}$ may be joined to form a five-, six-or seven-membered heterocycle containing at least one atom from the group consisting of N, P, O and S. The carboorganic radicals $R^{16A}$-$R^{20A}$ may also be substituted by halogens such as fluorine, chlorine or bromine, by amino $NR^{12A}_2$, by alkoxy and/or aryloxy $OR^{12A}$, for example dimethylamino, N-pyrrolidinyl, picolinyl, methoxy, ethoxy, or by Si-organic radicals $SiR^{11A}_3$. Further radicals $R^{16A}$-$R^{20A}$ are amino $NR^{12A}_2$, alkoxy and/or aryloxy $OR^{12A}$, halogens, and/or $SiR^{11A}_3$. The radicals $R^{11A}$ and $R^{12A}$ are more fully described above. Examples for possible radicals $R^{16A}$-$R^{20A}$ are dimethylamino, N-pyrrolidinyl, picolinyl, methoxy, ethoxy, isopropoxy, fluorine, chlorine, bromine or iodine. Si-organic radicals are for example trimethylsilyloxy, triethylsilyloxy, butyldimethylsilyloxy, tributylsilyloxy or tri-tert-butylsilyloxy, triallylsilyloxy, triphenylsilyloxy, or dimethylphenylsilyloxy.

Preferred radicals $R^{16A}$-$R^{20A}$ are hydrogen, methyl, trifluoromethyl, ethyl, n-propyl, iso-propyl, n-butyl, iso-butyl, tert.-butyl, n-pentyl, n-hexyl, n-heptyl, n-octyl, vinyl, allyl, benzyl, phenyl, fluorine, chlorine and bromine, especially hydrogen, wherein at least one of the radicals $R^{6A}$-$R^{10A}$ is a radical from the group consisting of chlorine, bromine, iodine, $CF_3$ or $OR^{12A}$.

Preferred radicals $R^{16A}$, $R^{18A}$ and $R^{20A}$ are methyl, trifluoromethyl, ethyl, n-propyl, iso-propyl, n-butyl, iso-butyl, tert.-butyl, n-pentyl, n-hexyl, n-heptyl, n-octyl, vinyl, allyl, benzyl, phenyl, fluorine, chlorine and bromine. In particular, $R^{20A}$ and/or $R^{18A}$ are $C_1$-$C_{22}$-alkyl, which may be substituted by halogen, i.e. methyl, trifluoromethyl, ethyl, n-propyl, n-butyl, n-pentyl, n-hexyl, n-heptyl, n-octyl, vinyl, wherein $R^{16A}$ is halogen, i.e. fluorine, chlorine or bromine, especially chlorine, or $R^{16A}$ and/or $R^{18A}$ is $C_1$-$C_{22}$-alkyl, which may be substituted by halogen, especially $C_1$-$C_{22}$-n-alkyl, which may be substituted by halogens, i.e. methyl, trifluoromethyl, ethyl, n-propyl, n-butyl, n-pentyl, n-hexyl, n-heptyl, n-octyl, vinyl, wherein $R^{20A}$ is halogen, i.e. fluorine, chlorine or bromine, especially chlorine. Preferred radicals $R^{17A}$ and $R^{19A}$ are hydrogen, methyl, ethyl, n-propyl, fluorine, chlorine and bromine, especially hydrogen. In particular, the radicals $R^{16A}$-$R^{20A}$ have the following meaning: $R^{20A}$ and $R^{18A}$ are independently of one another hydrogen, methyl, ethyl, n-propyl and iso-propyl, especially methyl, $R^{17A}$ and $R^{19A}$ are independently of one another hydrogen, methyl, ethyl and n-propyl, especially both are hydrogen, and $R^{16A}$ is fluorine, chlorine or bromine, especially chlorine.

Further preferred iron complexes of the invention are those of formula (Ib)

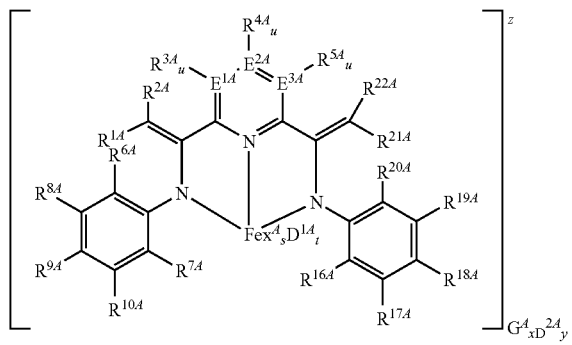

(Ib)

wherein the variables have the following meaning $R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11}_3$, wherein the organic radicals $R^{1A}$-$R^{2A}$ can also be substituted by halogens, and/or two radicals $R^{1A}$-$R^{2A}$ can also be bonded with one another to form a five-or six-membered ring, $R^{3A}$-$R^{10A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six-or seven-membered ring and/or in each case two radicals $R^{3A}$-$R^{5A}$ and/or in each case two radicals $R^{6A}$-$R^{10A}$ are bonded with one another to form a five-, six-or seven-membered heterocyclyl, which comprises at least one atom from the group consisting of N, P, O or S, wherein at least one of the radicals $R^{6A}$-$R^{10A}$ is selected from the group consisting of chlorine, bromine, iodine, $CF_3$ or $OR^{12A}$, $R^{11A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, and/or two radicals $R^{11A}$ can also be bonded with one another to form a five-or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five-or six-membered ring, $R^{21A}$-$R^{22A}$ independently of one another denote hydrogen, $C_1$-$C_{20}$-alkyl, $C_2$-$C_{20}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{21A}$-$R^{22A}$ can also be substituted by halogens, and/or in each case two radicals $R^{21A}$-$R^{22A}$ can also be bonded with one another to form a five-or six-membered ring, $R^{16A}$-$R^{20A}$ independently of one another denote hydrogen, $C_1$-$C_{22}$-alkyl, $C_2$-$C_{22}$-alkenyl, $C_s$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{16A}$-$R^{20A}$ can also be substituted by halogens, $NR^{12A}_2$, $OR^{12A}$ or $SiR^{11A}_3$ and/or in each case two radicals $R^{16A}$-$R^{20A}$ can also be bonded with one another to form a five-, six-or seven-membered ring and/or to form a five-, six-or seven-membered heterocyclyl, which comprises at least one atom from the group consisting of N, P, O or S, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, CN, SCN, β-diketonate, CO, $BF_4^-$, $PF_6^-$ or bulky non-coordinating anions, wherein the organic radicals $X^A$ can also be substituted by halogens and/or at least one radical $R^{13A}$, and the radicals $X^A$ are if appropriate bonded with one another, $R^{13A}$ independently of one another denote hydrogen, $C_1$-$C_{22}$-alkyl, $C_2$-$C_{22}$-alkenyl, $C_B$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogens, and/or in each case two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, wherein the organic radicals $R^{14A}$ can also be substituted by halogens, and/or in each case two radicals $R^{14A}$ can also be bonded with one another to form a five-or six-membered ring, s is 1, 2, 3 or 4, $D^{1A}$, $D^{2A}$ are a neutral donor, t, y are 0 to 4, and $G^A$ is a simply positively charged cation, x is 0, 1 or 2, and z is 0, −1 or −2.

The embodiments and preferred embodiments described above likewise apply to $E^{1A}$-$E^{3A}$, $R^{1A}$-$R^{2A}$, $R^{3A}$-$R^{10A}$, $R^{11A}$-$R^{14A}$, $R^{16A}$-$R^{20A}$, $D^{1A}$, $D^{2A}$, $X^A$, $G^A$, s, t, y, and u.

The radicals $R^{21A}$ and $R^{22A}$ can be independently of one another varied within a wide range. Possible carboorganic radicals $R^{21A}$-$R^{22A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5-to 7-membered cycloalkyl which may in turn bear a $C_1$-$C_{10}$-alkyl group and/or $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-or 2,6-dimethylphenyl, 2,3,4-, 2,3,5-, 2,3,6-, 2,4,5-, 2,4,6-or 3,4,5-trimethylphenyl, or arylalkyl having 1-10 C atoms in the alkyl radical and 6 to 20 C atoms in the aryl radical, which arylalkyl may be substituted by further alkyl groups, e.g. benzyl, o-, m-, p-methylbenzyl, 1-or 2-ethylphenyl, wherein two vicinal radicals $R^{21A}$-$R^{22A}$ may also be joined to form a 5-, 6-or 7-membered ring and/or two vicinal radicals $R^{16A}$-$R^{20A}$ may be joined to form a five-, six-or seven-membered heterocycle containing at least one atom from the group consisting of N, P, O and S, and/or the carboorganic radicals $R^{21A}$-$R^{22A}$ may also be substituted by halogens such as fluorine, chlorine or bromine. Furthermore, the radicals $R^{21A}$-$R^{22A}$ may also be $SiR^{11A}_3$. The radicals $R^{11A}$ have the same meaning as described above, i.e. trimethylsilyloxy, triethylsilyloxy, butyldimethylsilyloxy, tributylsilyloxy, tri-tert-butylsilyloxy, triallylsilyloxy, triphenylsilyloxy, or dimethylphenylsilyloxy.

Preferred radicals $R^{21A}$-$R^{22A}$ are hydrogen, methyl, ethyl, n-propyl, iso-propyl, n-butyl, iso-butyl, tert.-butyl, n-pentyl, n-hexyl, n-heptyl, n-octyl, benzyl, phenyl, ortho dialkyl-or dichlorosubstituted phenyl, trialkyl-or trichlorosubstituted phenyl, naphthyl, biphenyl and anthranyl, especially hydrogen and methyl. Preferably, $R^{21A}$-$R^{22A}$ are identical.

In particular, iron complexes of formula (Ia) and (Ib), wherein $R^{7A}$ and $R^{16A}$ are chlorine or bromine and $R^{6A}$, $R^{9A}$, $R^{18A}$ and $R^{20A}$ are methyl, ethyl, n-propyl, iso-propyl, n-butyl, iso-butyl and/or tert.-butyl are suitable as catalysts for the homo-and copolymerization or ethylene.

The iron complexes 1, 2, and 3 are especially preferred embodiments of the present invention.

complex 1

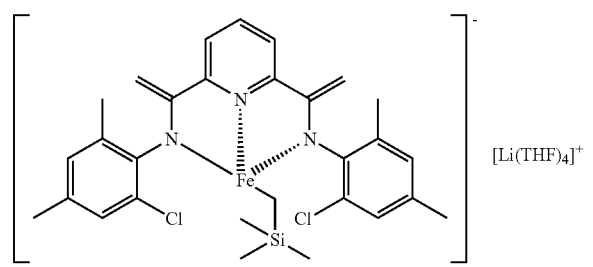

complex 2

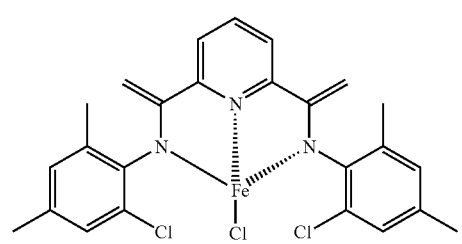

complex 3

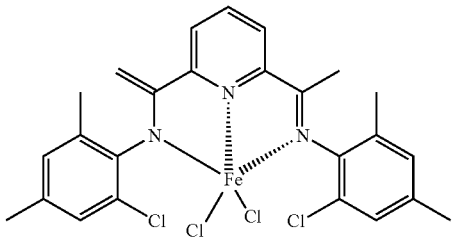

The iron complexes (A) of the invention are prepared for example likewise to the preparation of pyridine bis(enamido) iron complexes as described in J. Am. Chem. Soc. 127, 13019-13929. It is a transmetalation reaction between a charged ligand and an iron specie. The pyridine ligands are prepared according to WO 98/27124. It is a condensation reaction between a primary amine and a keton. The mono-and dideprotonated pyridine ligands used for this preparation are prepared likewise to Organometallics 2004, 23, 5054-61 and Organometallics 2002, 21, 3088-90. It is a deprotonation reaction between the neutral ligand and a strong base.

A further embodiment of the invention is a catalyst system for olefin polymerization, comprising at least one late transition metal complex (A') comprising at least one structural unit >C=C—N-M, wherein M is a late transition metal of any one of groups 8 to 12 of the Periodic Table of Elements, in combination with at least one activating compound (B), and/or at least one organic and/or inorganic support (C), and/or at least one further catalyst (D) suitable for olefin polymerization, and/or at least one metal compounds (E) of group 1, 2, or 13 of the Periodic Table of Elements. Preferred late transition metal complexes (A') are those of formula (I')

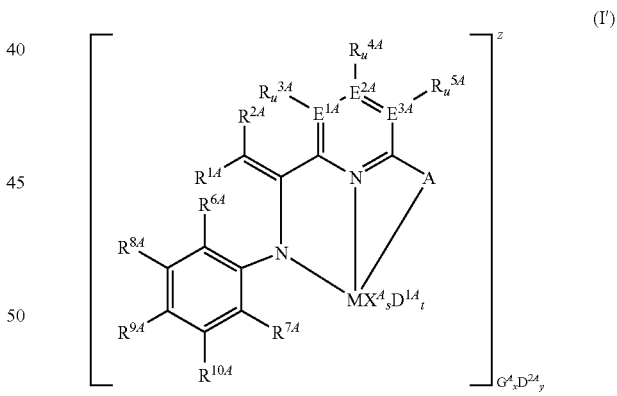

wherein the variables have the following meaning:
M is a late transition metal of any one of groups 8 to 12 of the Periodic Table of Elements, preferably Pd, Ni, Co or Fe, especially Co or Fe, A is

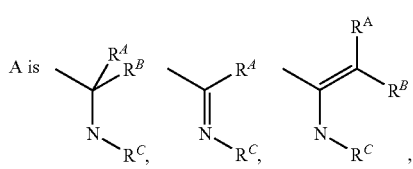

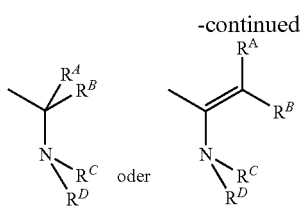

$R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical or $SiR^{11A}_3$, wherein the organic radicals $R^{1A}$-$R^{2A}$ can also be substituted by halogens and/or the two radicals $R^{1A}$-$R^{2A}$ can also be bonded with one another to form a five-or six-membered ring, $R^{3A}$-$R^{10A}$ independently of one another denote hydrogen, $C_1$-$C_{22}$-alkyl, $C_2$-$C_{22}$-alkenyl, $C_B$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six-or seven-membered heterocyclyl, which comprises at least one atom from the group consisting of N, P, O or S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six-or seven-membered ring and/or in each case two radicals $R^{3A}$-$R^{5A}$ and/or in each case two radicals $R^{6A}$-$R^{10A}$ are bonded with one another to form a five-, six-or seven-membered heterocyclyl, which comprises at least one atom from the group consisting of N, P, O or S, $R^{11A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, and/or two radicals $R^{11A}$ can also be bonded with one another to form a five-or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five-or six-membered ring, $R^A, R^B$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^A, R^B$ can also be substituted by halogens, and/or in each case two radicals $R^A, R^B$ can also be bonded with one another to form a five-or six-membered ring, $R^C, R^D$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^C, R^D$ can also be substituted by halogens, and/or in each case two radicals $R^C, R^D$ can also be bonded with one another to form a five-or six-membered ring, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, CN, SCN, β-diketonate, CO, $BF_4^-$, $PF_6^-$ or bulky non-coordinating anions, wherein the organic radicals $X^A$ can also be substituted by halogens and/or at least one radical $R^{13A}$, and the radicals $X^A$ are optionally bonded with one another, $R^{13A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogens, and/or in each case two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, wherein the organic radicals $R^{14A}$ can also be substituted by halogens, and/or in each case two radicals $R^{14A}$ can also be bonded with one another to form a five-or six-membered ring, s is 1, 2, 3 or 4, $D^{1A}, D^{2A}$ is a neutral donor, t, y is 0 to 4, $G^A$ is a simply positively charged cation, x is 0, 1 or 2, and z is 0, −1 or −2.

The variables are described in detail in the foregoing in connection with the iron complex (A). Especially preferred metal complexes in the catalyst systems of the invention are those of formulas (I), (Ia), and (Ib), in particular the preferred embodiments of these complexes described in the foregoing. Especially preferred are the complexes 1, 2 and 3.

The metal complexes (A) and/or (A') of the invention can be used by themselves or together with at least one further component described in more detail below as a catalyst system for olefin polymerization.

Optionally the metal complexes (A) and/or (A') can be brought into contact with at least one activating compound (B) in order to enhance polymerization activity. The at least one activating compound (B) can in each case be employed in any amount based on the metal complex (A) or (A'), preferably they are employed in an excess or in stoichiometric amounts. The amount of activating compound (B) to be used depends on the nature of the activator. The molar ratio of metal complex (A) and/or (A') to activating compound (B) is usually in the range of from 1:0.1 to 1:10000, preferably from 1:1 to 1:2000. Suitable activating compounds (B) are e.g. compounds of the type of aluminoxane, a strong neutral Lewis acid, an ionic compound having a Lewis acid cation or an ionic compound having a Broenstedt acid as a cation.

The compounds described in WO 00/31090 may for example be used as aluminoxanes. Particularly useful aluminoxanes are open-chain or cyclic aluminoxane compounds of the general formulas (II) or (III):

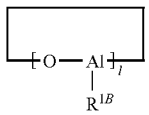

wherein $R^{1B}$-$R^{4B}$ are each, independently of one another, a $C_1$-$C_6$-alkyl group, preferably a methyl, ethyl, butyl or isobutyl group and I is an integer from 1 to 40, preferably from 4 to 25.

These oligomeric aluminoxane compounds are usually prepared by controlled reaction of a solution of a trialkylaluminum, in particular trimethylaluminum, with water. In general, the oligomeric aluminoxane compounds obtained are in the form of mixtures of both linear and cyclic chain molecules of various lengths, so that I is, o be regarded as a mean. The aluminoxane compounds can also be present in admixture with other metal alkyls, usually aluminum alkyls. Aluminoxane preparations suitable as activators are commercially available. Furthermore modified aluminoxanes in which some of the hydrocarbon radicals have been replaced by hydrogen atoms or alkoxy, aryloxy, siloxy or amide radicals can also be used in place of the aluminoxane compounds of the formula (II) or (III) as activators. It has been found to be advantageous to use the metal complexes (A) and/or (A') of the invention and the aluminoxane compounds in such amounts that the atomic ratio of aluminum from the aluminoxane compounds including any aluminum alkyl still present to the metal from the metal complexes (A) and/or (A') is in the range from 1:1 to 2000:1, preferably from 10:1 to 500:1 and in particular in the range from 20:1 to 400:1.

A particularly useful aluminoxane compound is methylaluminoxane.

A further class of suitable activators are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the metal from the metal complexes (A) and/or (A') is usually in the range from 1:1 to 100:1, preferably from 10:1 to 50:1 and in particular in the range from 20:1 to 40:1.

As strong, uncharged Lewis acids, preference is given to compounds of the general formula (IV)

$$M^{2B}X^{1B}X^{2B}X^{3B} \qquad (IV)$$

where $M^{2B}$ is an element of group 13 of the Periodic Table of Elements, in particular B, Al or Ga, preferably B, $X^{1B}$, $X^{2B}$ and $X^{3B}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl part and from 6 to 20 carbon atoms in the aryl part or fluorine, chlorine, bromine or iodine, in particular haloaryls, preferably pentafluorophenyl.

Further examples of strong, uncharged Lewis acids are given in WO 00/31090. Compounds which are particularly useful as activating compound (B) are boranes and boroxins such as trialkylborane, triarylborane or trimethylboroxin. Particular preference is given to using boranes which bear at least two perfluorinated aryl radicals. Particular preference is given to compounds of the general formula (IV) in which $X^{1B}$, $X^{2B}$ and $X^{3B}$ are identical, for example triphenylborane, tris(4-fluorophenyl)borane, tris(3,5-difluorophenyl)borane, tris(4-fluoromethylphenyl)borane, tris(pentafluorophenyl) borane, tris(tolyl)borane, tris(3,5-dimethylphenyl)borane, tris(3,5-difluorophenyl)borane or tris(3,4,5-trifluorophenyl) borane. Preference is given to using tris(pentafluorophenyl) borane. Suitable activating compounds (B) are preferably prepared by reaction of aluminum or boron compounds of the formula (IV) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl. Examples of combinations of compounds of the formula (IV) with Broenstedt acids are, in particular, trimethylaluminum/pentafluorophenol, trimethylaluminum/1-bis(pentafluorophenyl)methanol, trimethylaluminum/4-hydroxy-2,2',3,3',4',5,5',6,6'-nonafluorobiphenyl, triethylaluminum/pentafluorophenol and triisobutylaluminum/pentafluorophenol and triethylaluminum/4,4'-dihydroxy-2, 2',3,3',5,5',6,6'-octa-fluorobiphenyl hydrate. In further suitable aluminum and boron compounds of the formula (IV), $R^{1B}$ is an OH group, such as, for example, in boronic acids and borinic acids. Particular mention may be made of borinic acids having perfluorinated aryl radicals, for example $(C_6F_5)_2BOH$. Strong uncharged Lewis acids suitable as activating compounds (B) also include the reaction products of the reaction of a boronic acid with two equivalents of an aluminum trialkyl or the reaction products of the reaction of an aluminum trialkyl with two equivalents of an acidic fluorinated, in particular perfluorinated, carbon compound such as pentafluorophenol or bis(pentafluorophenyl)borinic acid.

Suitable ionic compounds having Lewis-acid cations include salt-like compounds of the cation of the general formula (V)

$$[((M^{3B})^{a+})Q_1Q_2\ldots Q_z]^{b+} \qquad (V) \text{ wherein}$$

$M^{3B}$ is an element of groups 1 to 16 of the Periodic Table of the Elements, $Q_1$ to $Q_z$ are simply negatively charged radicals such as $C_1$-$C_{28}$-alkyl, $C_6$-$C_{15}$-aryl, alkyl-aryl, arylalkyl, haloalkyl, haloaryl each having from 6 to 20 carbon atoms in the aryl part and from 1 to 28 carbon atoms in the alkyl part, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, b corresponds to the difference a-z, wherein b is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordi-nating counter ions, in particular boron compounds as are also mentioned in WO 91/09882, preferably tetrakis(pentafluorophenyl)borate. Salts having noncoordinating anions can also be prepared by combining a boron or aluminum compound, e.g. an aluminum alkyl, with a second compound which can react to link two or more boron or aluminum atoms, e.g. water, and a third compound which forms with the boron or aluminium compound an ionizing ionic compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added. Ionic compounds containing Broenstedt acids as cations preferably likewise have noncoordinating counter ions. As Broenstedt acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 9736937 are also suitable as activating compounds (B), in particular dimethylanilinium boratabenzenes or trityl boratabenzenes. Preferred ionic activating compounds (B) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate. It is also possible for two or more borate anions to be joined to one another, as in the dianion $[(C_6F_5)_2B—C_6F_4—B(C_6F_5)_2]^{2-}$, or the borate anion can be bound via a bridge to a suitable functional group on the support surface. Further suitable activating compounds (B) are listed in WO 00/31090. Suitable activating compounds (B) also include boron-aluminum compounds such as di[bis(pentafluorophenylboroxy)]methylalane. Examples of such boron-aluminum compounds are those disclosed in WO 99/06414.

The amount of strong, uncharged Lewis acids, ionic compounds having Lewis-acid cations or ionic compounds containing Broenstedt acids as cations is preferably from 0.1 to 20 equivalents, more preferably from 1 to 10 equivalents and particularly preferably from 1 to 2 equivalents, based on the metal complexes (A) and/or (A') of the invention. It is also possible to use mixtures of all the above-mentioned activating compounds (B). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane or a boroxin. Combinations of the preferred embodiments of the metal complexes (A) and/or (A') and the activating compounds (B) are particularly preferred.

A further possibility is to use an activating compounds (B) which can simultaneously be employed as support (C). Such systems are obtained, for example, from an inorganic oxide treated with zirconium alkoxide and subsequent chlorination, e.g. by means of carbon tetrachloride. The preparation of such systems is described, for example, in WO 01/41920.

In one embodiment of the invention, both the metal complexes (A) and/or (A') and the activating compounds (B) are used in a solvent, preferably an aromatic hydrocarbon having from 6 to 20 carbon atoms, in particular xylenes, toluene, pentane, hexane, heptane or a mixture thereof.

To enable the metal complexes (A) and/or (A') to be used in polymerization processes in the gas phase or in suspension, it is often advantageous to use the complexes in the form of a solid, i.e. for them to be applied to a solid support (C). Furthermore, the supported complexes have a high productivity. The metal complexes (A) and/or (A') can therefore also optionally be immobilized on an organic or inorganic support (C) and be used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polymers bearing polar functional groups, for example copolymers of ethene and acrylic esters, acrolein or vinyl acetate.

A preferred embodiment of the invention is a catalyst system comprising at least one metal complexes (A) and/or (A') according to the invention, at least one activating compound (B), and at least one support (C). To prepare the catalyst systems of the invention, preference is given to immobilizing the metal complexes (A) and/or (A') and/or the activating compound (B) on the support (C) by physisorption or else by means of a chemical reaction, i.e. covalent binding of the components, with reactive groups on the support surface. The order in which metal complexes (A) and/or (A'), activating compound (B) and support (C) are combined is in principle immaterial. After the individual process steps, the various intermediates can be washed with suitable inert solvents such as aliphatic or aromatic hydrocarbons. In a preferred embodiment, both components, metal complexes (A) and/or (A') and activator (B), are supported. The two components (A)/(A') and (B) can in this case be applied to different supports or together on a joint support. The components (A)/(A') and (B) are preferably applied to a joint support in order to ensure a relatively close spatial proximity of the various catalyst centres and thus to ensure good mixing of the different polymers formed.

Metal complexes (A) and/or (A') and activating compound (B) can be immobilized independently of one another, e.g. in succession or simultaneously. Thus, the support (C) can firstly be brought into contact with the activating compound or compounds (B) or the support (C) can firstly be brought into contact with the metal complexes (A) and/or (A') Preactivation of the metal complexes (A) and/or (A') by means of one or more activating compounds (B) prior to mixing with the support (C) is also possible. The metal complex (A) and/or (A') can, for example, be reacted simultaneously with the activating compound (B), or can be preactivated separately by means of the latter. In one possible embodiment, the metal complexes (A) and/or (A') can also be prepared in the presence of the support material. A further method of immobilization is prepolymerization of the catalyst system with or without prior application to a support. The immobilization is generally carried out in an inert solvent which can be removed by filtration or evaporation after the immobilization. After the individual process steps, the solid can be washed with suitably inert solvents such as aliphatic or aromatic hydrocarbons and dried. The supported catalyst is preferably obtained as a free-flowing powder. However, the use of the still moist, supported catalyst is also possible. Examples of the industrial implementation of the above process are described in WO 96/00243, WO 98/40419 or WO 00/05277.

As support (C), preference is given to using finely divided supports which can be any organic or inorganic solid. In particular, the support (C) can be a porous support such as talc, a sheet silicate such as montmorillonite, mica or an inorganic oxide or a finely divided polymer powder (e.g. polyolefin or a polymer having polar functional groups). The supports (C) used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 700 $m^2/g$, a pore volume in the range from 0.4 to 3.5 ml/g and a mean particle size in the range from 5 to 350 μm. Particular preference is given to supports having a specific surface area in the range from 200 to 550 $m^2/g$, a pore volume in the range from 0.5 to 3.0 ml/g and a mean particle size of from 10 to 150 μm.

The metal complexes (A) and/or (A') are preferably applied in such an amount that the concentration of the metal from the metal complexes (A) and/or (A') in the finished catalyst system is from 1 to 200 µmol, preferably from 5 to 100 µmol and particularly preferably from 10 to 70 µmol, per g of the finished catalyst system.

The support (C) can be subjected to a thermal treatment, e.g. to remove adsorbed water. Such a drying treatment is generally carried out at temperatures in the range from 50 to 1000° C., preferably from 100 to 600° C., with drying at from 100 to 200° C. preferably being carried out under reduced pressure and/or under a blanket of inert gas (e.g. nitrogen), or the support (C) can be calcined at temperatures of from 200 to 1000° C. to produce the desired structure of the solid and/or set the desired OH concentration on the surface. The support (C) can also be treated chemically using customary desiccants such as metal alkyls preferably aluminum alkyls, chlorosilanes or $SiCl_4$, or else methylaluminoxane. Appropriate treatment methods are described, for example, in WO 00/31090. The support (C) can also be chemically modified. For example, treatment of silica gel with $NH_4SiF_6$ or other fluorinating agents leads to fluorination of the silica gel surface, or treatment of silica gels with silanes containing nitrogen-, fluorine-or sulphur-containing groups leads to correspondingly modified silica gel surfaces.

Inorganic oxides suitable as support (C) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, $AlPO_4$, $ZrO_2$, $TiO_2$, $B_2O_3$ or mixtures thereof. Further preferred inorganic support materials are inorganic halides such as $MgCl_2$ or carbonates such as $Na_2CO_3$, $K_2CO_3$, $CaCO_3$, $MgCO_3$, sulphates such as $Na_2SO_4$, $Al_2(SO_4)_3$, $BaSO_4$, nitrates such as $KNO_3$, $Mg(NO_3)_2$ or $Al(NO_3)_3$.

As solid supports (C) for catalysts for olefin polymerization, preference is given to using silica gels since particles whose size and structure make them suitable as supports for olefin polymerization can be produced from this material. Spray-dried silica gels, which are spherical agglomerates of relatively small granular particles, i.e. primary particles, have been found to be particularly useful. The silica gels can be dried and/or calcined before use.

Further preferred supports (C) are hydrotalcites and calcined hydrotalcites. In mineralogy, hydrotalcite is a natural mineral having the ideal formula $Mg_6Al_2(OH)_{16}CO_3 \cdot 4H_2O$ whose structure is derived from that of brucite $Mg(OH)_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is balanced by the anions which are located together with water of crystallization in the layers in-between. Such sheet structures are found not only in magnesium-aluminum-hydroxides, but generally in mixed metal hydroxides of the general formula $$M(II)_{2x}^{2+}M(III)_2^{3+}(OH)_{4x+4} \cdot A_{2/n}^{n-} \cdot z\, H_2O \qquad (VI)$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is a number from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulphates, aryl ether sulphates or glycol ether sulphates, inorganic anions such as, in particular, carbonate, hydrogen carbonate, nitrate, chloride, sulphate or $B(OH)_4^-$ or polyoxometal anions such as $Mo_7O_{24}^{6-}$ or $V_{10}O_{28}^{6-}$. However, a mixture of a plurality of such anions is also possible. Accordingly, all such mixed metal hydroxides having a sheet structure should be regarded as hydrotalcites for the purposes of the present invention. Calcined hydrotalcites can be prepared from hydrotalcites by calcination, i.e. heating, by means of which, inter alia, the desired hydroxide group content can be set. In addition, the crystal structure also changes. Preferred calcined hydrotalcites are mixed oxides in which M(II) is magnesium and M(III) is aluminum. Such aluminum-magnesium mixed oxides are obtainable from Condea Chemie GmbH (now Sasol Chemie); Hamburg under the trade name Puralox Mg. Preference is also given to calcined hydrotalcites in which the structural transformation is complete or virtually complete. Calcination, i.e. transformation of the structure, can be confirmed, for example, by means of X-ray diffraction patterns. The metal complexes (A) and/or (A') are preferably applied in such an amount that the concentration of the metal from the metal complexes (A) and/or (A') in the finished catalyst system is from 1 to 100 µmol, preferably from 5 to 80 µmol and particularly preferably from 10 to 60 µmol, per g of finished catalyst system.

Organic support materials such as finely divided polyolefin powders (e.g. polyethylene, poly-propylene or polystyrene) can also be used as support (C) and are preferably likewise freed of adhering moisture, solvent residues or other impurities by appropriate purification and drying operations before use. It is also possible to use functionalized polymer supports, e.g. ones based on polystyrene, polyethylene, polypropylene or polybutylene, via whose functional groups, for example ammonium or hydroxy groups, at least one of the catalyst components can be immobilized. It is also possible to use polymer blends.

Optionally the catalyst system of the present invention can comprise further catalysts (D) suitable for olefin polymerization. Possible catalysts (D) here are, in particular, conventional Ziegler-Natta catalysts based on titanium, and conventional Phillips catalysts based on chromium compounds, in particular chromium oxides and metallocenes. So-called Ziegler catalyst components (as described e.g. in Falbe, J.; Regitz, M. (Hrsg.); Römpp Chemie Lexikon; $9^{th}$ ed.; Thieme; 1992; New York; vol. 6, p. 5128-5129) and/or metallocene catalyst components are preferred. Metallocene catalyst components are particularly preferred.

The Ziegler catalyst component is preferably a compound of a metal of group 4 (e.g. titanium, zirconium or hafnium), 5 (e.g. vanadium or niobium) or 6 (e.g. chromium or molybdenum) of the Periodic Table of the Elements. Halides, oxides, oxyhalides, hydroxides or alkoxides are preferred. Examples of Ziegler catalyst components which are given by way of example but are not limiting are titanium tetrachloride, zirconium tetrachloride, hafnium tetrachloride, titanium trichloride, vanadium trichloride, vanadium oxychloride, chromium trichloride or chromium oxide.

In the present application, metallocene catalyst components are understood as meaning cyclopentadienyl complexes which comprise one, two or three cyclopentadienyl ligands. In the present application, cyclopentadienyl ligand is understood as meaning any system which comprises a cyclic 5 membered ring system having 6 π electrons, such as, for example, indenyl or fluerenyl systems. Metallocene complexes of metals of group 3 and the lanthanoid group (e.g. lanthanum or yttrium) as well as metals of group 4 (e.g. titanium, zirconium or hafnium), 5 (e.g. vanadium or niobium) or 6 of the Periodic Table of the Elements (e.g. chromium or molybdenum) are preferred, and cyclopentadienyl complexes of titanium, zirconium or hafnium are particularly preferred. The cyclopentadienyl complexes can be e.g. bridged or non-bridged dicyclopentadienyl complexes, such as are described e.g. in EP 129 368, EP 561 479, EP 545 304 and EP 576 970 or monocyclopentadienyl complexes, such as bridged amidocyclopentadienyl complexes which are described e.g. in EP 416 815. Multinuclear cyclopentadienyl complexes are described e.g. in EP 632 063, π-ligand-substituted tetrahydropentalenes are described e.g. in EP 659 758 or π-ligand-substituted tetrahydroindenes are described e.g. in EP 661 300.

In particular, hafnocene catalyst components are useful as catalyst (D). Hafnocene catalyst components are understood as meaning e.g. cyclopentadienyl hafnium complexes of the general formula (VII).

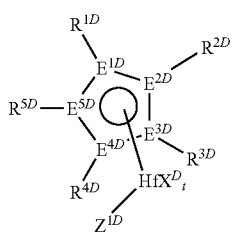

(VII)

wherein the radicals and indices have the following meaning:

$X^D$ independently of one another denotes, fluorine, chlorine, bromine, iodine, hydrogen, $C_1$-$C_{10}$-alkyl, $C_2$-$C_{10}$-alkenyl, $C_6$-$C_{15}$-aryl, alkylaryl having 1-10 carbon atoms in the alkyl part and 6 to 20 carbon atoms in the aryl part, —$OR^{6D}$ or —$NR^{6D}R^{7D}$, or two radicals $X^D$ form a substituted or unsubstituted diene ligand, in particular a 1,3-diene ligand, and the radicals $X^D$ are identical or not identical, and the radicals $X^D$ may be joined to one another, $E^{1D}$-$E^{5D}$ independently of one another denotes carbon, phosphor or nitrogen, wherein not more than one radical $E^{1D}$-$E^{5D}$ denotes phosphor or nitrogen, preferably all $E^{1D}$-$E^{5D}$ denote carbon, t is 1, 2 or 3, wherein t dependently of the oxidation level of hafnium has a value providing an uncharged metallocene complex of formula (VII), wherein $R^{6D}$ and $R^{7D}$ independently of one another denotes $C_1$-$C_{10}$-alkyl, $C_6$-$C_{15}$-aryl, alkylaryl, arylalkyl, fluoroalkyl or fluoroaryl each having 1 to 10 C-atoms in the alkyl part and 6 to 20 C-atoms in the aryl part, and $R^{1D}$ bis $R^{5D}$ independently of one another denote hydrogen, $C_1$-$C_{22}$-alkyl, 5-to 7-membered cycloalkyl or cycloalkenyl, which may be substituted by $C_1$-$C_{10}$-alkyl, $C_2$-$C_{22}$-alkenyl, $C_6$-$C_{22}$-aryl, arylalkyl having 1 to 16 C atoms in the alkyl radical and 6-21 C atoms in the aryl radical, $NR^{8D}_2$, $N(SiR^{8D}_3)_2$, $OR^{8D}$, $OSiR^{8D}_3$, $SiR^{8D}_3$, wherein the organic radicals $R^{1D}$-$R^{5D}$ can also be substituted by halogen and/or in each case two radicals $R^{1D}$-$R^{5D}$, especially vicinal radicals, can also be bonded with one another to form a five-, six- or seven-membered ring and/or to form a five-, six- or seven-membered heterocyclyl, which comprises at least one atom from the group consisting of N, P, O or S, where the radicals $R^{8D}$ can be identical or different and can each be $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy and $Z^{1D}$ is $X^D$ or

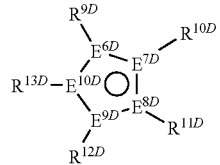

wherein the radicals $R^{9D}$ to $R^{13D}$ are each, independently of one another, hydrogen, $C_1$-$C_{22}$-alkyl, 5-to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{14D}_2$, $N(SiR^{14D}_3)_2$, $OR^{14D}$, $OSiR^{14D}_3$, $SiR^{14D}_3$, where the organic radicals $R^{9D}$-$R^{13D}$ may also be substituted by halogens and/or two radicals $R^{9D}$-$R^{13D}$, in particular vicinal radicals, may also be joined to form a five-, six-or seven-membered ring, and/or two vicinal radicals $R^{9D}$-$R^{13D}$ may be joined to form a five-, six-or seven-membered heterocycle containing at least one atom from the group consisting of N, P, O and S, where $R^{14D}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6D}$-$E^{10D}$ are each carbon or not more than one $E^{6D}$ to $E^{10D}$ is phosphorus or nitrogen, preferably carbon, or where the radicals $R^{4D}$ and $Z^{1D}$ together form an —$R^{15D}_v$-$A^{1D}$-group, where

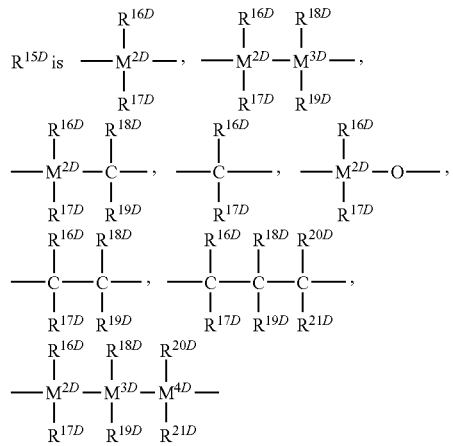

=$BR^{16D}$, =$BNR^{16D}R^{17D}$, =$AlR^{16D}$, —Ge—, —Sn—, —O—, —S—, =SO, =$SO_2$, =$NR^{16D}$, =CO, =$PR^{16D}$ or =$P(O)R^{16D}$, where $R^{16D}$-$R^{21D}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms, and
$M^{2D}$-$M^{4D}$ are each silicon, germanium or tin, or preferably silicon,
$A^{1D}$ is —O—, S>$NR^{22D}$, >$PR^{22D}$, =O, =S, =$NR^{22D}$, —O—$R^{22D}$, —$NR^{22D}{}_2$, —$PR^{22D}{}_2$ or an unsubstituted, substituted or fused, heterocyclic ring system, where
$R^{22B}$ are each, independently of one another, $C_1$-$C_{10}$-alkyl, $C_6$-$C_{15}$-aryl, $C_3$-$C_{10}$-cycloalkyl, $C_7$-$C_{18}$-alkylaryl or)Si $(R^{23D})_3$,
$R^{23D}$ is hydrogen, $C_1$-$C_{10}$-alkyl, $C_6$-$C_{15}$-aryl which may in turn bear $C_1$-$C_4$-alkyl groups as substituents or $C_3$-$C_{10}$-cycloalkyl,
v is 1 or when $A^{1D}$ is an unsubstituted, substituted or fused, heterocyclic ring system may also be 0
or where the radicals $R^{4D}$ and $R^{12D}$ together form an —$R^{15D}$ group.

$A^{1D}$ can, for example together with the bridge $R^{15D}$, form an amine, ether, thioether or phosphine. However, $A^{1D}$ can also be an unsubstituted, substituted or fused, heterocyclic aromatic ring system which can contain heteroatoms from the group consisting of oxygen, sulphur, nitrogen and phosphorus in addition to ring carbons. Examples of 5-membered heteroaryl groups which can contain from one to four nitrogen atoms and/or a sulphur or oxygen atom as ring members in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl and 1,2,4-triazol-3-yl. Examples of 6-membered heteroaryl groups which may contain from one to four nitrogen atoms and/or a phosphorus atom are 2-pyridinyl, 2-phosphabenzenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thionaphthenyl, 7-thionaphthenyl, 3-indazolyl, 7-indazolyl, 2-benzimidazolyl and 7-benzimidazolyl. Examples of benzo-fused 6-membered heteroaryl groups are 2-quinolyl, 8-quino-lyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, $3^{rd}$ revised edition, Verlag Chemie, Weinheim 1957.

The radicals $X^D$ in the general formula (VII) are preferably identical, preferably fluorine, chlorine, bromine, $C_1$-$C_7$-alkyl or aralkyl, in particular chlorine, methyl or benzyl.

The synthesis of such complexes can be carried out by methods known per se, with the reaction of the appropriately substituted cyclic hydrocarbon anions with halides of hafnium being preferred. Examples of appropriate preparative methods are described, for example, in Journal of Organometallic Chemistry, 369 (1989), 359-370.

The hafnocenes can be used in the Rac or pseudo-Rac form. The term pseudo-Rac refers to complexes in which the two cyclopentadienyl ligands are in the Rac arrangement relative to one another when all other substituents of the complex are disregarded. Examples of suitable hafnocenes as catalysts (D) are, inter alia, methylenebis(cyclopentadienyl) hafnium dichloride, methylenebis(3-methylcyclopentadienyl)hafnium dichloride, methylenebis(3-n-butylcyclopentadienyl)hafnium dichloride, methylenebis(indenyl)hafnium dichloride, methylenebis(tetrahydroindenyl)hafnium dichloride, isopropylidenebis(cyclopentadienyl)hafnium dichloride, isopropylidenebis(3-trimethylsilylcyclopentadienyl) hafnium dichloride, isopropylidenebis(3-methylcyclopentadienyl)hafnium dichloride, isopropylidenebis(3-n-butylcyclopentadienyl)hafnium dichloride, isopropylidenebis(3-phenylcyclopentadienyl) hafnium dichloride, isopropylidenebis(indenyl)hafnium dichloride, isopropylidene-bis(tetrahydroindenyl)hafnium dichloride, dimethylsilanediylbis(cyclopentadienyl)hafnium dichloride, dimethylsilanediylbis(indenyl)hafnium dichloride, dimethylsilanediylbis(tetrahydroindenyl)-hafnium dichloride, ethylenebis(cyclopentadienyl)hafnium dichloride, ethylenebis(indenyl)hafnium dichloride, ethylenebis(tetrahydroindenyl)hafnium dichloride, tetramethylethylene-9-fluorenyl-cyclopentadienylhafnium dichloride, dimethylsilanediylbis(tetramethylcyclopentadienyl)hafnium dichloride, dimethylsilanediylbis(3-trimethylsilylcyclopentadienyl)hafnium dichloride, dimethyl-silanediylbis(3-methylcyclopentadienyl)hafnium dichloride, dimethylsilanediylbis(3-n-butylcyclo-pentadienyl)hafnium dichloride, dimethylsilanediylbis(3-tert-butyl-5-methylcyclopentadienyl)-hafnium dichloride, dimethylsilanediylbis(3-tert-butyl-5-ethylcyclopentadienyl)hafnium dichloride, dimethylsilanediylbis(2-methylindenyl)hafnium dichloride, dimethylsilanediylbis(2-isopropylinde-nyl)hafnium dichloride, dimethylsilanediylbis(2-tert-butylindenyl)hafnium dichloride, diethylsilane-diylbis(2-methylindenyl)hafnium dibromide, dimethylsilanediylbis(3-methyl-5-methylcyclo-penta-dienyl)hafnium dichloride, dimethylsilanediylbis(3-ethyl-5-isopropylcyclopentadienyl)hafnium dichloride, dimethylsilanediylbis(2-ethylindenyl)hafnium dichloride, dimethylsilanediylbis(2-methyl-4,5-benzindenyl)hafniurn dichloride, dimethylsilanediylbis(2-ethyl-4,5-benzindenyl) hafnium dichloride, methylphenylsilanediylbis(2-methyl-4, 5-benzindenyl)hafnium dichloride, methylphenyl-silanediylbis(2-ethyl-4,5-benzindenyl)hafnium dichloride, diphenylsilanediylbis(2-methyl-4,5-benzindenyl)hafnium dichloride, diphenylsilanediylbis(2-ethyl-4,5-benzindenyl) hafnium dichloride, diphenylsilanediylbis(2-methylindenyl) hafnium dichloride, dimethylsilanediylbis(2-methyl-4-phe-nylindenyl)hafnium dichloride, dimethylsilanediylbis(2-ethyl-4-phenylindenyl)hafnium dichloride, dimethylsilanediylbis(2-methyl-4-(1-naphthyl)indenyl) hafnium dichloride, dimethylsilanediylbis(2-ethyl-4-(1-naphthyl)indenyl)hafnium dichloride, dimethylsilanediylbis (2-propyl-4-(1-naphthyl)-indenyl)hafnium dichloride, dimethylsilanediylbis(2-i-butyl-4-(1-naphthyl)indenyl) hafnium dichlo-ride, dimethylsilanediylbis(2-propyl-4-(9-phenanthryl)indenyl)hafnium dichloride, dimethylsilane-diylbis(2-methyl-4-isopropylindenyl)hafnium dichloride, dimethylsilanediylbis(2,7-dimethyl-4-isopropylindenyl) hafnium dichloride, dimethylsilanediylbis(2-methyl-4,6-di-isopropylindenyl)-hafnium dichloride, dimethylsilanediylbis (2-methyl-4[p-trifluoromethylphenyl]indenyl)hafnium dichloride, dimethylsilanediylbis(2-methyl-4-[3',5'-dimethylphenyl]indenyl)hafnium dichloride, dimethylsilanediylbis (2-methyl-4-[4'-tert-butylphenyl]indenyl)hafnium dichloride, diethylsilanediyl-bis(2-methyl-4-[4'-tert-butylphenyl]indenyl)hafnium dichloride, dimethylsilanediylbis(2-ethyl-4-[4'-tert-butylphenyl]indenyl)hafnium dichloride, dimethylsilanediylbis(2-propyl-4-[4'-tert-butyl-phenyl]indenyl)hafnium dichloride, dimethylsilanediylbis(2-isopropyl-4-[4'-tert-butylphenyl]-indenyl)hafnium dichloride, dimethylsilanediylbis(2-n-butyl-4-[4'-tert-butylphenyl]indenyl)hafnium dichloride, dimethylsilanediylbis(2-hexyl-4-[4'-tert-butylphenyl]indenyl)hafnium dichloride, dimethylsilanediyl(2-isopropyl-4-phenylindenyl)(2-methyl-4-phenylindenyl)hafnium dichloride, dimethylsilanediyl(2-isopropyl-4-(1-naphthyl)indenyl)(2-methyl-4-(1-naphthyl)indenyl)hafnium dichloride, dimethylsilanediyl(2-isopropyl-4-[4'-tert-butylphenyl]indenyl)(2-methyl-4-[4'tert-butylphenyl]indenyl)hafnium dichloride, dimethylsilanediyl(2-isopropyl-4-[4'-tert-butylphenyl]-indenyl)(2-ethyl-4-[4'-tert-butylphenyl]indenyl)hafnium dichloride, dimethylsilanediyl(2-isopropyl-4-[4'-tert-butylphenyl]indenyl)(2-methyl-4-[3',5'bis-tert-butylphenyl]indenyl)hafnium dichloride, dimethylsilanediyl(2-isopropyl-4-[4'-tert-butylphenyl]indenyl)(2-methyl-4-[1'-naphthyl]indenyl)-hafnium dichloride and ethylene(2-isopropyl-4-[4'-tert-butylphenyl]indenyl)(2-methyl-4-[4'tert-butylphenyl]indenyl)hafnium dichloride, and also the corresponding dimethylhafnium, monochloro-mono(alkylaryloxy)hafnium and di(alkylaryloxy)hafnium compounds. The complexes can be used in the rac form, the meso form or as mixtures of these.

Among the hafnocenes of the general formula (VII), those of the formula (VIII)

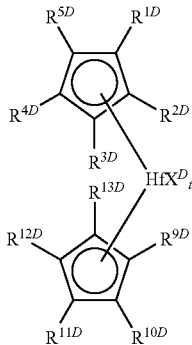

(VIII)

are preferred.

Among the compounds of the formula (VIII), preference is given to those in which $X^D$ is fluorine, chlorine, bromine, $C_1$-$C_4$-alkyl or benzyl, or two radicals $X^D$ form a substituted or unsubstituted butadiene ligand, t is 1 or 2, preferably 2, $R^{1D}$ to $R^{5D}$ are each hydrogen, $C_1$-$C_8$-alkyl, $C_6$-$C_8$-aryl, $NR^{8D}_2$, $OSiR^{8D}_3$ or $Si(R^{8D})_3$ and $R^{9D}$ to $R^{13D}$ are each hydrogen, $C_1$-$C_8$-alkyl or $C_6$-$C_8$-aryl, $NR^{14D}_2$, $OSiR^{14D}_3$ or $Si(R^{14D})_3$ or in each case two radicals $R^{1D}$ to $R^{5D}$ and/or $R^{9D}$ to $R^{13D}$ together with the $C_5$ ring form an indenyl, fluorenyl or substituted indenyl or fluorenyl system.

The hafnocenes of the formula (VIII) in which the cyclopentadienyl radicals are identical are particularly useful. Examples of particularly suitable catalysts (D) of the formula (VIII) are, inter alia: bis(cyclopentadienyl)hafnium dichloride, bis(indenyl)hafnium dichloride, bis(fluorenyl)hafnium dichloride, bis(tetrahydroindenyl)hafnium dichloride, bis(pentamethylcyclopentadienyl)hafnium dichloride, bis(trimethylsilylcyclopentadienyl)hafnium dichloride, bis(trimethoxysilylcyclopenta-dienyl)hafnium dichloride, bis(ethylcyclopentadienyl)hafnium dichloride, bis(isobutylcyclopenta-dienyl)hafnium dichloride, bis(3-butenylcyclopentadienyl)hafnium dichloride, bis(methylcyclo-pentadienyl)hafnium dichloride, bis(1,3-di-tert-butylcyclopentadienyl)hafnium dichloride, bis(trifluoromethylcyclopentadienyl)hafnium dichloride, bis(tert-butylcyclopentadienyl)hafnium dichloride, bis(n-butylcyclopentadienyl)hafnium dichloride, bis(phenylcyclopentadienyl)hafnium dichloride, bis(N,N-dimethylaminomethylcyclopentadienyl)hafnium dichloride, bis(1,3-dimethyl-cyclopentadienyl)hafnium dichloride, bis(1-n-butyl-3-methylcyclopentadienyl)hafnium dichloride, (cyclopentadienyl)(methylcyclopentadienyl)hafnium dichloride, (cyclopentadienyl)(n-butylcyclo-pentadienyl)hafnium dichloride, (methylcyclopentadienyl)(n-butylcyclo-pentadienyl)hafnium dichloride, (cyclopentadienyl)(1-methyl-3-n-butylcyclopentadienyl)hafnium dichloride, bis(tetra-methylcyclopentadienyl)hafnium dichloride and also the corresponding dimethylhafnium compounds. Further examples are the corresponding hafnocene compounds in which one or two of the chloride ligands have been replaced by bromide or iodide.

The molar ratio of metal complexes (A) and/or (A') to olefin polymerization catalyst (D) is usually in the range from 1:100 to 100:1, preferably from 1:10 to 10:1 and particularly preferably from 1:5 to 5:1. The activation of the metal complexes (A) and/or (A') and of the transition metal complex (D) of the catalyst composition can be carried out using the same activating compound (B) or activator mixture or different activators.

It is often advantageous to use the same activating compound (B) for both the catalysts (A)/(A') and (D). Suitable activating compounds (B) which are able to react with the metal complexes (A) and/or (A') or the transition metal complex (D) to convert it into a catalytically active or more active compound are, for example, compounds such as those described above. In particular, compounds such as an aluminoxane, a strong uncharged Lewis acid, an ionic compound having a Lewis-acid cation or an ionic compound containing a Broenstedt acid as cation are suitable.

The activating compounds (B) can in each case be used in any amounts based on the complexes (A)/(A') and (D) of the catalyst composition of the invention. They are preferably used in an excess or in stoichiometric amounts, in each case based on the complex (A)/(A') or (D) which they activate. The amount of activating compound(s) to be used depends on the type of the activating compound (B). In general, the molar ratio of metal complexes (A) and/or (A') to activating compound (B) can be from 1:0.1 to 1:10000, preferably from 1:1 to 1:2000. Also the molar ratio of transition metal complex (D) to activating compound (B) is also usually in the range from 1:0.1 to 1:10000, preferably from 1:1 to 1:2000.

Preferably aluminoxane is used as joint activating compound (B) for both catalysts components (A)/(A') and (D). Preference is also given to the combination of salt-like compounds of the cation of the general formula (V), in particular N,N-dimethylanilinium tetrakis(pentafluorophenyl)borate, N,N-dimethylcyclohexylammonium tetrakis(pentafluorophenyl)borate, N,N-dimethylbenzylammonium tetrakis(pentafluorophenyl)borate or trityl tetrakispentafluorophenylborate, as activator (B) for hafnocenes (D), in particular in combination with an aluminoxane as activating compound (B) for the metal complexes (A) and/or (A'). Combinations of the preferred embodiments of (B) with the preferred embodiments of (A)/(A') and/or (D) are particularly preferred. Further particularly useful joint activating compounds (B) are the reaction products of aluminum compounds of the formula (IV) with perfluorinated alcohols and phenols. Particular preference is given to a catalyst system comprising at least one metal complex (A) and/or (A') at least one transition metal complex (D), at least one activating compound (B) and at least one support (C).

A preferred catalyst composition according to the invention comprises one or more supports (C). It is possible for both the metal complexe (A) and/or (A') and the catalyst (D) to be supported, or only one of the two components can be supported. In a preferred embodiment, both the components (A)/(A') and (D) are supported. The two components (A)/(A') and (D) can in this case be applied to different supports or together on a joint support. The components (A)/(A') and (D) are preferably applied to a joint support in order to ensure a relatively close spatial proximity of the various catalyst centres and thus to ensure good mixing of the different polymers formed. To prepare the catalyst systems of the invention, preference is given to immobilizing one of the components (A)/(A') and one of the components (D) and/or activating compound (B) or the support (C) by physisorption or else by means of a chemical reaction, i.e. covalent binding of the components, with reactive groups on the support surface. The order in which metal complexes (A) and/or (A'), activating compound (B), support (C), and transition metal complex (D) are combined is in principle immaterial. After the individual process steps, the various intermediates can be washed with suitable inert solvents such as aliphatic or aromatic hydrocarbons.

Metal complexes (A) and/or (A') activating compound (B) and the transition metal complex (D) can be immobilized independently of one another, e.g. in succession or simultaneously. Thus, the support (C) can firstly be brought into contact with the activating compound or compounds (B) or the support (C) can firstly be brought into contact with the metal complexes (A) and/or (A') and/or the transition metal complex (D). Preactivation of the metal complexes (A) and/or (A') by means of one or more activating compounds (B) prior to mixing with the support (C) is also possible. The metal complexes (A) and/or (A') can, for example, be reacted simultaneously with the transition metal complex (D) with the activating compound (B), or can be preactivated separately by means of the latter. The preactivated metal complexes (A) and/or (A') can be applied to the support (C), before or after the preactivated transition metal complex (D). In one possible embodiment, the metal complexes (A) and/or (A') and/or the transition metal complex (D) can also be prepared in the presence of the support (C). A further method of immobilization is prepolymerization of the catalyst system with or without prior application to a support (C). The immobilization is generally carried out in an inert solvent which can be removed by filtration or evaporation after the immobilization. After the individual process steps, the solid can be washed with suitably inert solvents such as aliphatic or aromatic hydrocarbons and dried. However, the use of the still moist, supported catalyst is also possible.

In a preferred method of preparing the supported catalyst system, at least one metal complex (A) and/or (A') is brought into contact with an activated compound (B) and subsequently mixed with the dehydrated or passivated support (C). The transition metal complex (D) is likewise brought into contact with at least one activating compound (B) in a suitable solvent, preferably giving a soluble reaction product, an adduct or a mixture. The preparation obtained in this way is then mixed with the immobilized iron complex, which is used directly or after the solvent has been separated off, and the solvent is completely or partly removed. The resulting supported catalyst system is preferably dried to ensure that all or most of the solvent is removed from the pores of the support material. The supported catalyst is preferably obtained as a free-flowing powder. Examples of the industrial implementation of the above process are described in WO 96/00243, WO 98/40419 or WO 00/05277. A further preferred embodiment comprises firstly producing the activating compound (B) on the support (C) and subsequently bringing this supported compound into contact with the metal complex (A) and/or (A') and the transition metal complex (D).

The catalyst system may further comprise, as additional component a metal compound (E) of the general formula (IX),

$$M^E(R^{1E})_{r^E}(R^{2E})_{s^E}(R^{3E})_{t^E} \quad \text{(IX) wherein}$$

$M^E$ is Li, Na, K, Be, Mg, Ca, Sr, Ba, boron, aluminum, gallium, indium, thallium, zinc, in particular Li, Na, K, Mg, boron, aluminum or Zn, $R^{1E}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{2E}$ and $R^{3E}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl part and from 6 to 20 carbon atoms in the aryl part, or alkoxy together with $C_1$-$C_{10}$-alkyl or $C_6$-$C_{15}$-aryl, $r^E$ is an integer from 1 to 3, and $s^E$ and $t^E$ are integers from 0 to 2, with the sum $r^E+s^E+t^E$ corresponding to the valence of $M^E$, wherein the metal compound of formula (IX) is usually not identical to the activating compound (B). It is also possible to use mixtures of various metal compounds of the formula (IX). Among the metal compounds of the general formula (IX), preference is given to those in which $M^E$ s lithium, magnesium, boron or aluminum and $R^{1E}$ is $C_1$-$C_{20}$-alkyl.

Particularly preferred metal compounds of the formula (IX) are methyl lithium, ethyl lithium, n-butyl lithium, methyl magnesium chloride, methyl magnesium bromide, ethyl magnesium chloride, ethyl magnesium bromide, butyl magnesium chloride, dimethyl magnesium, diethyl magnesium, dibutyl magnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound (IX) is used, it is preferably present in the catalyst system in such an amount that the molar ratio of $M^E$ from formula (IX) to metal from the metal complex (A) and/or (A') is from 3000:1 to 0.1:1, preferably from 800:1 to 0.2:1 and particularly preferably from 100:1 to 1:1.

In general, the metal compound of the general formula (IX) is used as constituent of a catalyst system for the polymerization or copolymerization of olefins. Here, the metal compound (IX) can, for example, be used for preparing a catalyst solid comprising the support (C) and/or be added during or shortly before the polymerization. The metal compounds (IX) used can be identical or different. It is also possible, particularly when the catalyst solid contains no activating component (B), for the catalyst system to further comprise, in addition to the catalyst solid, one or more activating compounds (B) which are identical to or different from any compounds (IX) present in the catalyst solid.

The component (IX) can likewise be reacted in any order with the metal complex (A) and/or (A') and optionally with the activating compound (B) and the support (C). The metal complex (A) and/or (A') can, for example, be brought into contact with the component(s) (B) and/or (C) either before or after being brought into contact with the olefins to be polymerized. Preactivation by means of one or more activating compound (B) prior to mixing with the olefin and further addition of the same or another activating compound (B) and/or (C) after this mixture has been brought into contact with the olefin is also possible. Preactivation is generally carried out at temperatures of 10-100° C., preferably 20-80° C. In another preferred embodiment, a catalyst solid is prepared from a metal complex (A) and/or (A') an activating compound (B), and a support (C) as described above and this is brought into contact with the metal compound (IX) during, at the commencement of or shortly before the polymerization. Preference is given to firstly bringing the metal compound (IX) into contact with the 1-olefin to be polymerized and subsequently adding the catalyst solid comprising a metal complex (A) and/or (A') an activating compound (B), and a support (C) as described above. In a further, preferred embodiment, the support (C) is firstly brought into contact with the metal compound (IX), and the metal complex (A) and/or (A') and any further activating compound (B) are then dealt with as described above.

It is also possible for the catalyst system firstly to be prepolymerized with 1-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to a monomer polymerized onto it is usually in the range from 1:0.1 to 1:1000, preferably from 1:1 to 1:200. Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to metal complexes (A) and/or (A') is usually from 1:1000 to 1000:1, preferably from 1:5 to 20:1.

The metal complex (A) and/or (A' is preferably applied in such an amount that the concentration of metal from the metal complex (A) and/or (A') in the finished catalyst system is from 1 to 200 μmol, preferably from 5 to 100 μmol and particularly preferably from 10 to 70 μmol, per g of support (C). The transition metal complex (D) is preferably applied in such an amount that the concentration of transition metal from the transition metal complex (D) in the finished catalyst system is from 1 to 200 μmol, preferably from 5 to 100 μmol and particularly preferably from 10 to 70 μmol, per g of support (C).

As solid supports (C) for catalysts for olefin polymerization, preference is given to using silica gels since particles whose size and structure make them suitable as supports for olefin polymerization can be produced from this material. Spray-dried silica gels, which are spherical agglomerates of relatively small granular particles, i.e. primary particles, have been found to be particularly useful. The silica gels can be dried and/or calcined before use.

A further embodiment of the invention is a process for the polymerization of olefins in the presence of the catalyst composition of the invention. The present catalyst composition and the present catalyst system are especially useful for the preparation of homo-and copolymers of ethylene.

In the copolymerization process of the invention, ethylene is polymerized with α-olefins having from 3 to 12 carbon atoms. Preferred 1-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene. Particularly preferred 1-olefins are $C_4$-$C_{12}$-1-alkenes, in particular linear $C_6$-$C_{10}$-1-alkenes. It is also possible to polymerize mixtures of various 1-olefins. Preference is given to polymerizing at least one α-olefin selected from the group consisting of ethene, propene, 1-butene, 1-pentene, 1-hexene, 1-heptene, 1-octene and 1-decene. Monomer mixtures containing at least 50 mol % of ethene are preferably used.

The process of the invention for polymerizing ethylene or copolymerizing ethylene with 1-olefins can be carried out using all industrially known polymerization methods at temperatures in the range from −60 to 350° C., preferably from 0 to 200° C. and particularly preferably from 25 to 150° C., and under pressures of from 0.5 to 4000 bar, preferably from 1 to 100 bar and particularly preferably from 3 to 40 bar. The mean residence times are usually from 0.5 to 5 hours, preferably from 0.5 to 3 hours. The advantageous pressure and temperature ranges for carrying out the polymerizations usually depend on the polymerization method. The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes and gas-phase fluidized-bed processes are all possible.

In the case of high-pressure polymerization processes, which are customarily carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. In the case of low-pressure polymerization processes, it is usual to set a temperature which is at least a few degrees below the softening temperature of the polymer. In particular, temperatures of from 50 to 180° C., preferably from 70 to 120° C., are set in these polymerization processes. In the case of suspension polymerizations, the polymerization is usually carried out in a suspension medium, preferably an inert hydrocarbon such as isobutane or mixtures of hydrocarbons or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out either batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out in the range from 30 to 125° C. at pressures of from 1 to 50 bar.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed mode, in which part of the circulating gas is cooled to below the dew point and is recirculated as a two-phase mixture to the reactor. Furthermore, it is possible to use a multizone reactor in which the two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example as in the Hostalen® process. A parallel reactor arrangement using two or more identical or different processes is also possible. Furthermore, molar mass regulators, for example hydrogen, or customary additives such as antistatics can also be used in the polymerizations. To obtain the high proportions of vinyl groups, the polymerization is preferably carried out with smaller amounts or no hydrogen present.

The polymerization is preferably carried out in a single reactor, in particular in a gas-phase reactor. The polymerization of ethylene with α-olefins having from 3 to 12 carbon atoms gives the polyethylene of the invention when the catalyst of the invention is used. The polyethylene powder obtained directly from the reactor displays a very high homogeneity, so that, unlike the case of cascade processes, subsequent extrusion is not necessary in order to obtain a homogeneous product. The preparation of the polyethylene of the invention in the reactor reduces the energy consumption, requires no subsequent blending processes and makes simple control of the molecular mass distributions and the molecular mass fractions of the various polymers possible. In addition, good mixing of the polyethylene is achieved.

The present metal complexes (A) and/or (A'), especially the iron complexes (A), and catalyst systems are new high reactive catalysts which can preferably be used for the homo- and copolymerization of olefins, especially of ethylene. These metal complexes (A) and/or (A'), preferably the iron complexes (A), and especially preferably the complexes 1, 2 and 3, of the invention are particularly advantageous for the preparation of low molecular weight components of multimodal products, especially bimodal products. A multimodal product has at least a bimodal molecular mass distribution that means, for the purposes of the present patent application, that the molecular mass distribution has at least two points of inflection on one flank starting from a maximum. A monomodal molecular mass distribution means that the molecular mass distribution has a single maximum.

By use of the metal complexes (A) and/or (A') of the invention, especially by use of the preferred embodiments, it is possible to prepare low molecular mass homo-and copolymers of ethylene having a monomodal molecular mass distribution. In particular, polyethylenes having a molecular mass $M_w$ of not more than 100 000 can be prepared. Preferably, polyethylenes having a molecular mass $M_w$ of not more than 50 000, especially of not more than 40 000, more preferably between 5000 and 35000, can be prepared. The ratio between weight average molecular mass $M_w$ and number average molecular mass $M_n$, the polydispersity index Q, of the polyethylenes prepared by use of the metal complexes (A) and/or (A'), especially by use of the iron complexes (A) and in particular by use of the complexes 1, 2 and 3, of the invention is not higher than 25, preferably not higher than 20. In particular, the polydispersity index Q, is between 5 and 18, preferably between 5 and 15.

Homo-and copolymers of ethylene and mixtures of both can be prepared according to the described processes by use of the metal complexes (A) and/or (A') of the present invention as active component of catalyst systems, especially of the above described preferred catalyst systems. The molecular mass distribution of the polyethylenes prepared according to the invention can be monomodal, bimodal or multimodal. In particular, the molecular mass distribution is monomodal or bimodal. Especially, polyethylenes having a molecular mass $M_w$ of not more than 1 000 000 can be prepared. It is preferably possible to prepare polyethylenes having a molecular mass $M_w$ of not more than 500 000, especially of not more than 300 000, more preferably between 70 000 and 250 000. The polydispersity index Q, of polyethylenes producible by use of catalyst systems comprising metal complexes (A) and/or (A'), preferably metal complexes (A), especially complexes 1, 2 and 3, of the present invention is not higher than 50, preferably not higher than 30, especially preferred not higher than 25. Even more preferred is a polydispersity index 0, between 5 and 25.

The polyethylenes prepared by use of the metal complexes and catalyst systems of the present invention, especially by use of the preferred embodiments, can be used for producing fibers, films and moldings.

EXAMPLES

The following examples illustrate the invention without restricting the scope of the invention.

All synthesis and polymerizations were conducted under argon atmosphere. All solvents were flushed with argon and dried over molecular sieves before use.

The measured values described were determined in the following way:

The determination of the intrinsic viscosity [η], the limit of viscosity number by extrapolation of polymer concentration to zero was carried out in accordance with EN ISO 1628-1, at 130° C. by means of an automatic Ubbelohde viscometer (Lauda PVS 1) with decalin as solvent.

The determination of the molecular mass distributions and the $M_w$, $M_n$, and $Q=M_w/M_n$ derived there from was carried out by means of high-temperature gel permeation chromatography on a WATERS 150 C using a method based on DIN 55672-1 and the following columns connected in series: 3× SHODEX AT 806 MS, 1× SHODEX UT 807 and 1× SHODEX AT-G under the following conditions: solvent: 1,2,4-trichlorobenzene (stabilized with 0.025% by weight of 2,6-di-tert-butyl-4-methylphenol), flow: 1 ml/min, 500 μl injection volume, temperature: 135° C., calibration using polyethylene Standards. Evaluation was carried out using WIN-GPC(HSEntwicklungsgesell-schaft far wissenschaftliche Hard-and Software mbH, Ober-Hilbersheim).

The density [g/cm³] was determined in accordance with ISO 1183.

Abbreviations in the table below:

[η] intrinsic viscosity t(poly) polymerization time polymer amount of polymer pol. polymerization density polymer density compl. iron complex cat. catalyst eq equivalent activ. productivity of the catalyst in g of polymer obtained per g of catalyst used per hour MAO methyl aluminoxane IPRA isoprenyl aluminoxane THF tetrahydrofuran $M_w$ weight average molecular mass $M_n$ number average molecular mass $Q=M_w/M_n$ polydispersity index Preparation of the Ligand

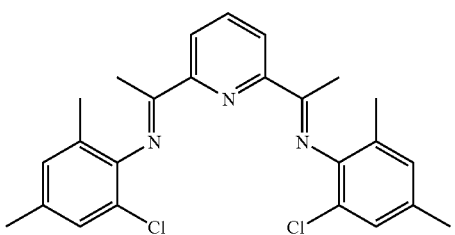

Diacetylpyridine (35 g, 0.214 mmol, 1 eq), 2,4-dimethyl-6-chloroaniline (76.77 g, 0.493 mmol, 2.3 eq) and Sicapent (45 g) were dissolved at 25° C. in THF (1200 ml). The solution was thus refluxed during 20 h. After 20 h under reflux additional quantities of aniline (25 g) and Sicapent (25 g) were added. After 40 h under reflux, the yellow suspension was filtered and the cake was washed with THF (2×75 ml). The mother liquor was concentrated in order to remove 85% to 90% of the THF. Then MeOH (430 ml) was added. The obtained suspension was heated to 45° C. and filtered at the same temperature. The yellow powder on the frit was washed with MeOH (2×50 ml) at 25° C. and dried under vacuum. 68.7 g of a yellow powder was collected (73% regarding diacetylpyridine).

$^1$H-NMR, CDCl$_3$: 8.49 (d, 2H, pyr), 7.92 (t, 1H, pyr), 7.12 (brs, 2H, Ar), 6.96 (brs, 2H, Ar), 2.31 (s, 12H, 4×CH$_3$ Ar), 2.08 (s, 6H, 2×CH$_3$ imine).

Preparation of Iron Complexes (a)

Example 1

Preparation of Complex 1

A solution of Me$_3$SiCH$_2$Li/1M in pentane (1.79 ml, 1.79 mmol, 2.1 eq) was added dropwise under stirring to a suspension of FeCl$_2$ (THF)$_{1.5}$ (0.2 g, 0.85 mol, 1 eq) in diethyl ether (15 ml) at −30° C. After 30 minutes of stirring at −30° C. a solution of monodeprotonated ligand [[2,6-((4,6-(Me)$_2$-2-Cl—C$_6$H$_5$)N═C(CH$_3$)][2,6-((4,6-(Me)$_2$-2-Cl—C$_6$H$_5$)N═C(CH$_3$)]-C$_5$H$_3$N]Li (0.38 g, 0.85 mol, 1 eq) (prepared in 2 steps according to Organometallics 2002, 21, 3088-90: 1—addition of MeLi (1 eq) to the ligand in diethyl ether at 25° C.; 2—the latter was stirred in toluene under reflux during 15 minutes, concentration and dilution in diethyl ether) in diethyl ether (10 ml) also kept at −30° C. was added. After 1 h at −30° C., the suspension was allowed to stir to 25° C. and filtered. The solvent was concentrated and the residue was dissolved in THF. Addition of hexane under stirring afforded a suspension which was filtered. The brown powder was dried under vacuum and collected (0.34 g, 48%).

Example 2

Preparation of Complex 2

A solution of Me$_3$SiCH$_2$Li/1M in pentane (2.28 ml, 2.28 mmol, 2 eq) was added drop by drop at 25° C. to a solution of 2,6-((4,6-(Me)$_2$-2-Cl—C$_6$H$_5$)N═C(CH$_3$))$_2$—C$_5$H$_3$N (0.5 g, 1.14 mmol) in THF (8 ml). After 1 hour of stirring, a solution of FeCl$_3$ (0.184 g, 1.14 mmol, 1 eq) in THF (8 ml) was added to the dideprotonated ligand at room temperature. The mixture was stirred at room temperature overnight. After evaporation of the solvent, the resulting residue was extracted with toluene (2×15 mL) and filtered to remove LiCl. Toluene was concentrated to 5 g and stored overnight at 0° C. The precipitate was filtered and dried under vacuum to lead a green powder of complex 2 (0.509 g, 85%).

Example 3

Preparation of Complex 3

A solution of lithium diisopropylamide (2M/THF, 0.29 mL, 0.57 mmol, 1 eq) was added drop by drop at −30° C. to a solution of 2,6-((4,6-(Me)$_2$-2-lC-C$_6$H$_5$)N═C(CH$_3$))$_2$—C$_5$H$_3$N (0.25 g, 0.57 mmol, 1 eq) in diethyl ether (5 ml). As soon as the addition was done, the reaction was stirred at room temperature during 1 hour. Then, a solution of FeCl$_3$ (0.092 g, 0.57 mmol, 1 eq) in diethyl ether (5 ml) was added to the monodeprotonated ligand at room temperature. The mixture was stirred at room temperature overnight. After evaporation of the solvent, the resulting residue was washed twice with diethyl ether (2×2.5 ml) and dried under vacuum (the mother liquor was discarded). The green powder was then extracted with CH$_2$Cl$_2$ and filtered to remove LiCl. CH$_2$Cl$_2$ was evaporated and the residue was triturated with pentane. The suspension was filtered and dried under vacuum to lead a green powder of complex 3 (0.09 g, 30%).

Polymerization Process A by Means of Complexes 1-3

Polymerization examples 1-9 comprising catalysts 1-3 were conducted in a 1 l-4-necked flask connected with a contact thermometer, Teflon blade stirrer, gas inlet tube, condenser and heating mantle. 250 ml of toluene were provided in this flask, and the corresponding amounts of complexes were added under argon at 40° C. The solution was heated up to 75° C. for 10 minutes to totally dissolve the complex. Then the solution was cooled down to 40° C. and the corresponding amount of a methyl aluminoxane solution (MAO, 4.75 M in toluene, Crompton) as described in Table 1 was added. 10 to 40 l/h of ethylene were piped through the solution depending on the consumption. Hydrogen was piped through this solution in such an amount that it corresponded to ¼ of the ethylene flow. 1-Hexene was added, starting with 10 ml. After 5 minutes, 1 ml 1-hexene per minute was added, until 13 ml in total had been added. The ethylene addition was stopped to end the polymerization and argon was piped through the solution. MAO was totally decomposed by addition of a mixture of 15 ml concentrated hydrochloric acid and 50 ml methanol. After 15 minutes of stirring, 250 ml methanol were added, whereby the polymer precipitated completely. The polymer was filtered off by a glass filter frit, washed with methanol three times and dried in vacuum at 70° C. All polymerization data and product data are summarized in Table 1.

TABLE 1

| Polymerization | Monomer/Regulator | Compl. [mg] | Compl. [μmol] | MAO [mmol] | Compl.: Al | t(Poly) [min] | Polymer [g] | Activity [kgPE/mol*h] | [η] [dl/g] | $M_w$ | Q |
|---|---|---|---|---|---|---|---|---|---|---|---|
| Pol. 1 (Compl. 1) | C2/— | 17.5 | 19.98 | 9.99 | 500 | 20 | 2 | 300 | 0.6 | 31495 | 10.4 |

TABLE 1-continued

| Polymerization | Monomer/Regulator | Compl. [mg] | Compl. [μmol] | MAO [mmol] | Compl.: Al | t(Poly) [min] | Polymer [g] | Activity [kgPE/mol*h] | [η] [dl/g] | $M_w$ | Q |
|---|---|---|---|---|---|---|---|---|---|---|---|
| Pol. 2 (Compl. 2) | C2/— | 16 | 30.32 | 15.16 | 500 | 10 | 4.2 | 950 | 0.35 | 9727 | 7.37 |
| Pol. 3 (Compl. 3) | C2/— | 10.5 | 18.61 | 9.305 | 500 | 10 | 3.6 | 1161 | 0.36 | 14552 | 7.14 |
| Pol. 4* (Compl. 1) | C2 + C6/— | 17.8 | 20.32 | 10.16 | 500 | 20 | 4.3 | 635 | 0.35 | 11147 | 8.67 |
| Pol. 5* (Compl. 2) | C2 + C6/— | 12.2 | 23.12 | 11.56 | 500 | 20 | 4.8 | 623 | 0.49 | 12250 | 7.02 |
| Pol. 6* (Compl. 3) | C2 + C6/— | 12.2 | 21.63 | 10.815 | 500 | 20 | 3.6 | 499 | 0.58 | 11549 | 7.46 |
| Pol. 7* (Compl. 1) | C2 + C6/H2 | 13 | 14.84 | 7.42 | 500 | 15 | 2.7 | 728 | 0.54 | 17054 | 7.4 |
| Pol. 8* (Compl. 2) | C2 + C6/H2 | 11.8 | 22.36 | 11.18 | 500 | 15 | 4.6 | 823 | 0.18 | 8462 | 5.06 |
| Pol. 9* (Compl. 3) | C2 + C6/H2 | 11.5 | 20.38 | 10.19 | 500 | 15 | 4.2 | 824 | 0.43 | 10283 | 6.34 |

*Copolymerization with 1-hexene 13 ml

Preparation of Catalysts 1-3

Example 4

Complex 2 was immobilized on a $SiO_2$ support to form catalyst 1. For that purpose, spray dried silica (XPO 2326, Grace) was heated for 6 hours at 600 C for pre-treatment. Subsequently, a mixture of 5.5 mg of complex 2, 0.25 ml MAO (4.75 M in toluene, Crompton, 895 mmol), and 2.5 ml toluene was stirred for 30 minutes at room temperature, 0.35 g of the pre-treated support material were added while still stirring and the resulting mixture was stirred for additional 2 hours at room temperature. The molar ratio of iron to aluminum was 1:100. The solid was dried under reduced pressure until it was free-flowing. 0.4 g of catalyst 1 was obtained.

Example 5

Complex 3 was immobilized on a $SiO_2$ support according to example 4 to form catalyst 2. For that purpose, a mixture of 18.2 mg of complex 3, 0.7 ml MAO (0.85 M in toluene, Crompton, 895 mmol), and 1 ml toluene was used together with 1.2 g of the pre-treated support material. The molar ratio of iron to aluminum was 1:100. The solid was dried under reduced pressure until it was free-flowing. 2 g of catalyst 2 were obtained.

Polymerization Process B by Means of Catalysts 1 and 2

The polymerization examples with the catalysts 1 and 2 were conducted in a 1 l-gas autoclave. 100 g of polymer seeds (HDPE sieved>1 mm and heated at 80° C. for 6 hours) were placed in the autoclave. The autoclave was evacuated and the pressure was enhanced to 1.013 bar with argon. 1 ml of a solution of Costelan® AS 100 (from Costenoble) in heptane (50 mg/ml) and 4 ml of a solution of IPRA in heptane (50 mg/ml) were added. Then the corresponding amounts of catalysts were added under argon. Afterwards, argon was pressed on up to 10 bar and ethylene up to 20 bar. Optionally, 1-hexene was continuously added in a ratio of 0.07 ml to 1 l ethylene. Optionally, hydrogen was continuously added in a ratio of 3 ml to 1 l ethylene. The pressure was maintained at 20 bar for 60 minutes. Then the pressure was reduced during 5 minutes to 0 mbar. The inside temperature was kept at 70° C. during the whole reaction. Then the product was sieved (sieve 0.5 mm). All polymerization and product data are summarized in Table 2.

TABLE 2

| Polymerization | 1-Hexene [ml] | Regulator $H_2$ [ml] | Catalyst [mg] | Polymer [g] | Activity [g/g] | [η] [dl/g] | $M_w$ | Q |
|---|---|---|---|---|---|---|---|---|
| 10 (Catalyst 1) | 0 | 0 | 180 | 35 | 195 | 3.44 | 228359 | 56.16 |
| 11 (Catalyst 2) | 0 | 0 | 176 | 54 | 307 | 1.24 | 74917 | 17.64 |
| 12 (Catalyst 2) | 7 | 0 | 204 | 47 | 230 | 1.11 | 51391 | 11.24 |
| 13 (Catalyst 2) | 0 | 205 | 174 | 82 | 471 | 1.49 | 85577 | 17.2 |

Preparation of Hybrid Catalyst

Example 6

An iron complex and a hafnocene were immobilized on a $SiO_2$ support according to example 4 to form catalyst 3. For that purpose, a mixture of 11.15 mg (0.02 mmol) of complex 3, 39.2 mg (0.08 mmol) bis(n-butylcyclopentadienyl) hafnium dichloride, 1.7 ml MAO (4.75 M in toluene, Crompton, 895 mmol) and 1 ml toluene was used together with 1.3 g of the pre-treated support. The molar ratio of (iron+hafnium) to aluminum was 1:100. The solid was dried under reduced pressure until it was free-flowing. 2 g of catalyst 3 were obtained.

Polymerization Process C

The polymerization examples with the catalysts 1 and 3 were conducted in a 1 l-gas autoclave. 100 g of polymer seeds (HDPE sieved>1 mm and heated at 80° C. for 6 hours) were placed in the autoclave. The autoclave was evacuated and the pressure was raised to 1.013 bar with argon. 1 ml of a solution of Costelan® AS 100 (from Costenoble) in heptane (50 mg/ml) and 4 ml of a solution of IPRA in heptane (50 mg/ml) were added. Then the corresponding amounts of catalysts were added under argon. Afterwards, argon was pressed on up to 10 bar and then ethylene up to 20 bar. Optionally, 1-hexene was continuously added in a ratio of 0.07 ml to 1 l ethylene. Optionally, hydrogen was continuously added in a ratio of 3 ml to 1 l ethylene. The pressure was maintained at 20 bar for 60 minutes. Then the pressure was reduced during 5 minutes to 0 mbar. The inside temperature was kept at 70° C. during the whole reaction. Finally, the product was sieved (sieve 0.5 mm). All polymerization and product data are summarized in Table 3.

TABLE 3

| Polymerization | 1-Hexene [ml] | Regulator H$_2$ [ml] | Catalyst [mg] | Polymer [g] | Activity [g/g] | [η] [dl/g] | M$_w$ | Q |
|---|---|---|---|---|---|---|---|---|
| 14 (catalyst 3) | 0 | 0 | 191 | 109 | 571 | 3.13 | 238335 | 24.51 |
| 15 (catalyst 1) | 0 | 0 | 185 | 85 | 459 | 1.01 | 49657 | 16.15 |
| 16 (catalyst 3) | 8 | 0 | 205 | 60 | 293 | 1.61 | 105352 | 22.5 |

The invention claimed is:

1. Iron complex (A) of formula (Ia):

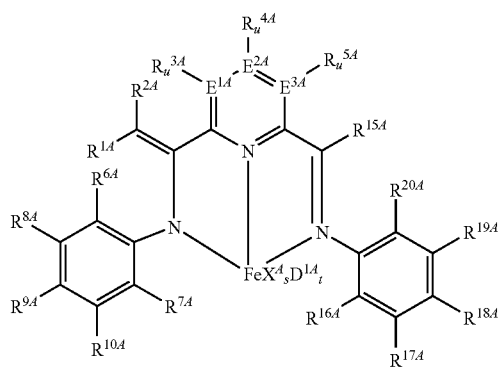

(Ia)

wherein the variables have the following meaning:

$R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11}_3$, wherein the organic radicals $R^{1A}$-$R^{2A}$ can also be substituted by halogens, and/or two radicals $R^{1A}$-$R^{2A}$ can also be bonded with one another to form a five- or six-membered ring, $R^{3A}$-$R^{10A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six- or seven-membered heterocyclyl, which comprises at least one atom selected from the group consisting of N, P, O and S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six- or seven-membered ring and/or in each case two radicals $R^{3A}$-$R^{5A}$ and/or in each case two radicals $R^{6A}$-$R^{10A}$ are bonded with one another to form a five-, six- or seven-membered heterocyclyl, which comprises at least one atom selected from the group consisting of N, P, O and S, wherein at least one of the radicals $R^{6A}$-$R^{10A}$ is selected from the group consisting of chlorine, bromine, iodine, $CF_3$ and $OR^{12A}$, $R^{11A}$ independently of one another denote hydrogen, $C_1$-$C_{22}$-alkyl, $C_2$-$C_{22}$-alkenyl, $C_6$-$C_{22}$-aryl, or arylalkyl having 1 to 10 C atoms in the alkyl radical and 6 to 20 C atoms in the aryl radical, wherein two radicals $R^{11A}$ can also be bonded with one another to form a five- or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five- or six-membered ring, $R^{15A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^{15A}$ can also be substituted by halogens, $R^{16A}$-$R^{20A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six- or seven-membered heterocyclyl, which comprises at least one atom selected from the group consisting of N, P, O and S, wherein the organic radicals $R^{16A}$-$R^{20A}$ can also be substituted by halogens, $NR^{12A}_2$, $OR^{12A}$ or $SiR^{11A}_3$ and/or in each case two radicals $R^{16A}$-$R^{20A}$ can also be bonded with one another to form a five-, six- or seven-membered ring and/or to form a five-, six- or seven-membered heterocyclyl, which comprises at least one atom selected from the group consisting of N, P, O and S, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, CN, SCN, β-diketonate, CO, $BF_4^-$, $PF_6^-$ or bulky non-coordinating anions, wherein the organic radicals $X^A$ can also be substituted by halogens and/or at least one radical $R^{13A}$, and the radicals $X^A$ are optionally bonded with one another, $R^{13A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogens, and/or two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, or arylalkyl having 1 to 10 C atoms in the alkyl radical and 6 to 20 C atoms in the aryl radical, wherein the organic radicals $R^{14A}$ can also be substituted by halogens, and/or two radicals $R^{14A}$ can also be bonded with one another to form a five-or six-membered ring, s is 1, 2, 3 or 4, t is 0 to 4, and $D^{1A}$ is a neutral donor.

2. Iron complex (A) of formula (Ia), according to claim 1, wherein $R^{6A}$ is chlorine or bromine.

3. Catalyst system for polymerization of olefins, comprising at least one iron complex (A) of formula (Ia) according to claim 1, in combination with at least one activator (B), and/or at least one organic and/or inorganic support (C), and/or at least one further catalyst (D) suitable for olefin polymerization, and /or at least one metal compounds (E) of group 1, 2, or 13 of the Periodic Table of Elements.

4. Prepolymerized catalyst system, comprising the catalyst system according to claim 3 and one or more linear $C_2$-$C_{10}$-1-alkenes polymerized onto it in a mass ratio of from 1:0.1 to 1:1000.

5. A process which comprises polymerizing or copolymerizing ethylene and a 1-olefin in the presence of the iron complex according to claim 1.

6. A process which comprises polymerizing or copolymerizing ethylene and a 1-olefin in the presence of the catalyst system according to claim 3.

7. Process for preparing polyolefins by polymerization or copolymerization of olefins in the presence of an iron complex according to claim 1.

8. Process for preparing polyolefins by polymerization or copolymerization of olefins in the presence of a catalyst system according to claim 3.

9. A method comprising preparing a fiber, film, or molding using a polyolefin prepared according to the process of claim 8.

10. Iron complex (A) of formula (Ib):

(Ib)

wherein the variables have the following meaning $R^{1A}$-$R^{2A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11}_3$, wherein the organic radicals $R^{1A}$-$R^{2A}$ can also be substituted by halogens, and/or two radicals $R^{1A}$-$R^{2A}$ can also be bonded with one another to form a five-or six-membered ring, $R^{3A}$-$R^{5A}$, $R^{8A}$ and $R^{10A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six- or seven-membered heterocyclyl, which comprises at least one atom selected from the group consisting of N, P, O or S, wherein the organic radicals $R^{3A}$-$R^{10A}$ can also be substituted by halogens, $NR^{12A}_2$, $OR^{12A}$ or $SiR^{11A}_3$ and/or in each case two radicals $R^{3A}$-$R^{5A}$ and/or in each case two radicals $R^{6A}$-$R^{10A}$ can also be bonded with one another to form a five-, six-or seven-membered ring and/or in each case two radicals $R^{3A}$-$R^{5A}$ and/or in each case two radicals $R^{6A}$-$R^{10A}$ are bonded with one another to form a five-, six-or seven-membered heterocyclyl, which comprises at least one atom selected from the group consisting of N, P, O or S, wherein at least one of the radicals $R^{6A}$-$R^{10A}$ is selected from the group consisting of chlorine, bromine, iodine, $CF_3$ or $OR^{12A}$, $R^{11A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, and/or two radicals $R^{11A}$ can also be bonded with one another to form a five-or six-membered ring, $R^{12A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{11A}_3$, wherein the organic radicals $R^{12A}$ can also be substituted by halogens, and/or in each case two radicals $R^{12A}$ can also be bonded with one another to form a five-or six-membered ring, $R^{21A}$-$R^{22A}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6 to 20 C atoms in the aryl radical, or $SiR^{11A}_3$, wherein the organic radicals $R^{21A}$-$R^{22A}$ can also be substituted by halogens, and/or in each case two radicals $R^{21A}$-$R^{22A}$ can also be bonded with one another to form a five-or six-membered ring, $R^{17A}$ and $R^{19A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, $NR^{12A}_2$, $OR^{12A}$, halogen, $SiR^{11A}_3$ or five-, six- or seven-membered heterocyclyl, which comprises at least one atom selected from the group consisting of N, P, O or S, wherein the organic radicals $R^{16A}$-$R^{20A}$ can also be substituted by halogens, $NR^{12A}_2$, $OR^{12A}$ or $SiR^{11A}_3$ and/or in each case two radicals $R^{16A}$-$R^{20A}$ can also be bonded with one another to form a five-, six- or seven-membered ring and/or to form a five-, six-or seven-membered heterocyclyl, which comprises at least one atom selected from the group consisting of N, P, O or S, $E^{1A}$-$E^{3A}$ independently of one another denote carbon or nitrogen, u independently of one another are 0 for $E^{1A}$-$E^{3A}$ as nitrogen and 1 for $E^{1A}$-$E^{3A}$ as carbon, $X^A$ independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6 to 20 C atoms in the aryl radical, $NR^{13A}_2$, $OR^{13A}$, $SR^{13A}$, $SO_3R^{13A}$, $OC(O)R^{13A}$, CN, SCN, β-diketonate, CO, $BF_4^-$, $PF_6^-$ or bulky non-coordinating anions, wherein the organic radicals $X^A$ can also be substituted by halogens and/or at least one radical $R^{13A}$, and the radicals $X^A$ are, if appropriate, bonded with one another, $R^{13A}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6 to 20 C atoms in the aryl radical, or $SiR^{14A}_3$, wherein the organic radicals $R^{13A}$ can also be substituted by halogens, and/or in each case two radicals $R^{13A}$ can also be bonded with one another to form a five-or six-membered ring, $R^{14A}$ independently of one another denote hydrogen, $C_1$-$C_{20}$-alkyl, $C_2$-$C_{20}$-alkenyl, $C_6$-$C_{20}$-aryl, or arylalkyl having 1 to 10 C atoms in the alkyl radical and 6 to 20 C atoms in the aryl radical, wherein the organic radicals $R^{14A}$ can also be substituted by halogens, and/or in each case two radicals $R^{14A}$ can also be bonded with one another to form a five-or six-membered ring, s is 1, 2, 3 or 4,
$D^{1A}$, $D^{2A}$ are a neutral donor,
t, y are 0 to 4, and
$G^A$ is a simply positively charged cation,
x is 0, 1 or 2, and
z is 0, −1 or −2,
wherein $R^{7A}$ and $R^{16A}$ are chlorine or bromine and $R^{6A}$, $R^{9A}$, $R^{18A}$ and $R^{20A}$ are methyl, ethyl, n-propyl, isopropyl, n-butyl, isobutyl or tert-butyl.

11. A catalyst system for polymerization of olefins, comprising at least one iron complex (A) of formula (Ib) according to claim 10, in combination with at least one activator (B), and/or at least one organic and/or inorganic support (C), and/or at least one further catalyst (D) suitable for olefin polymerization, and/or at least one metal compounds (E) of group 1, 2, or 13 of the Periodic Table of Elements.

12. A prepolymerized catalyst system, comprising the catalyst system according to claim 11 and one or more linear $C_2$-$C_{10}$-1-alkenes polymerized onto it in a mass ratio of from 1:0.1 to 1:1000.

13. A process which comprises polymerizing or copolymerizing ethylene and a 1-olefin in the presence of the iron complex according to claim 10.

14. A process which comprises polymerizing or copolymerizing ethylene and a 1-olefin in the presence of the catalyst system according to claim 11.

15. A process for preparing polyolefins by polymerization or copolymerization of olefins in the presence of an iron complex according to claim 10.

16. A process for preparing polyolefins by polymerization or copolymerization of olefins in the presence of a catalyst system according to claim 11.

17. A process comprising preparing a fiber, film, or molding using a polyolefin prepared according to the process of claim 16.

* * * * *